US008049018B2

(12) United States Patent
Dan-Oh et al.

(10) Patent No.: US 8,049,018 B2
(45) Date of Patent: Nov. 1, 2011

(54) METHINE DYES AND USES OF THE SAME

(75) Inventors: Yasufumi Dan-Oh, Okayama (JP);
Masahiko Toki, Okayama (JP); Kentaro Yano, Okayama (JP); Yasushi Aizawa, Okayama (JP)

(73) Assignee: Kabushiki Kaisha Hayashibara Seibutsu Kagaku Kenkyujo, Okayama (JP)

( * ) Notice: Subject to any disclaimer, the term of this patent is extended or adjusted under 35 U.S.C. 154(b) by 494 days.

(21) Appl. No.: 12/293,066

(22) PCT Filed: Nov. 7, 2006

(86) PCT No.: PCT/JP2006/322149
§ 371 (c)(1),
(2), (4) Date: Sep. 15, 2008

(87) PCT Pub. No.: WO2007/105336
PCT Pub. Date: Sep. 20, 2007

(65) Prior Publication Data
US 2009/0076278 A1    Mar. 19, 2009

(30) Foreign Application Priority Data

Mar. 13, 2006  (JP) ................................. 2006/304913

(51) Int. Cl.
*C07D 209/60*   (2006.01)
(52) U.S. Cl. ..................................................... 548/427
(58) Field of Classification Search .................... 548/427
See application file for complete search history.

(56) References Cited

U.S. PATENT DOCUMENTS
7,632,945 B2 * 12/2009 Shinpo et al. .................. 544/64

FOREIGN PATENT DOCUMENTS

| EP | 1103547 A1 | | 3/2005 |
|----|------------|---|--------|
| JP | 116611 | | 5/1989 |
| JP | 254991 A | | 11/1991 |
| JP | 058961 A | | 3/1999 |
| JP | 344750 A | | 12/2000 |
| JP | 202592 | | 7/2002 |
| JP | 167343 | | 6/2003 |
| JP | 231359 A | | 8/2003 |
| JP | 2004-53799 A | * | 2/2004 |
| JP | 053799 A | | 2/2004 |
| WO | 0075111 A1 | | 12/2000 |

OTHER PUBLICATIONS

"Kanko-Shikiso (Photosynthesizing Dyes)", edited by Hayami et al., Sangyo Tosho., Japan. pp. 24-30 (1997).
Majer, J.R. "Dyes Containing The Indole Ring-II", Tetrahedron, 9:111-115 (1960).
Hunig, S. et al., "Uber zweistufige Redoxsysteme, XXI, Synthese vinyloger und azavinyloger Redoxsysteme mit Indolylresten als Endgruppen", Justus Liebigs Annalen der Chemie, No. 6, pp. 1039-1059 (1976).
"Shikizai-Kogaku-Handbook" (Handbook for Color Material Technology), 1st edition, Asakura Publishing Co., Ltd., Japan. pp. 1274-1282 (1989).
"Senryo-to-Yakuhin (Dyes and Chemicals) ", Edited by Masahiro Shinkai et al., Japan, vol. 37, pp. 185-197 (1992).

* cited by examiner

*Primary Examiner* — Joseph Kosack
(74) *Attorney, Agent, or Firm* — Browdy and Neimark, PLLC

(57) ABSTRACT

The present invention provides novel organic compounds, which absorb the light in the ultra violet and the infrared regions, have improved light tolerance and solubility in solvents, and have thermal tolerance suitable for uses to which the organic compounds are applied, and provides uses of the same. The above objects are solved by providing indolenine compounds and methine dyes, which have a bis-indolenine skeleton composed of two indolenine rings linked together at their respective C-3 positions via a divalent linking group, and by providing optical recording media containing the methine dyes.

4 Claims, 3 Drawing Sheets

[FIG. 1]
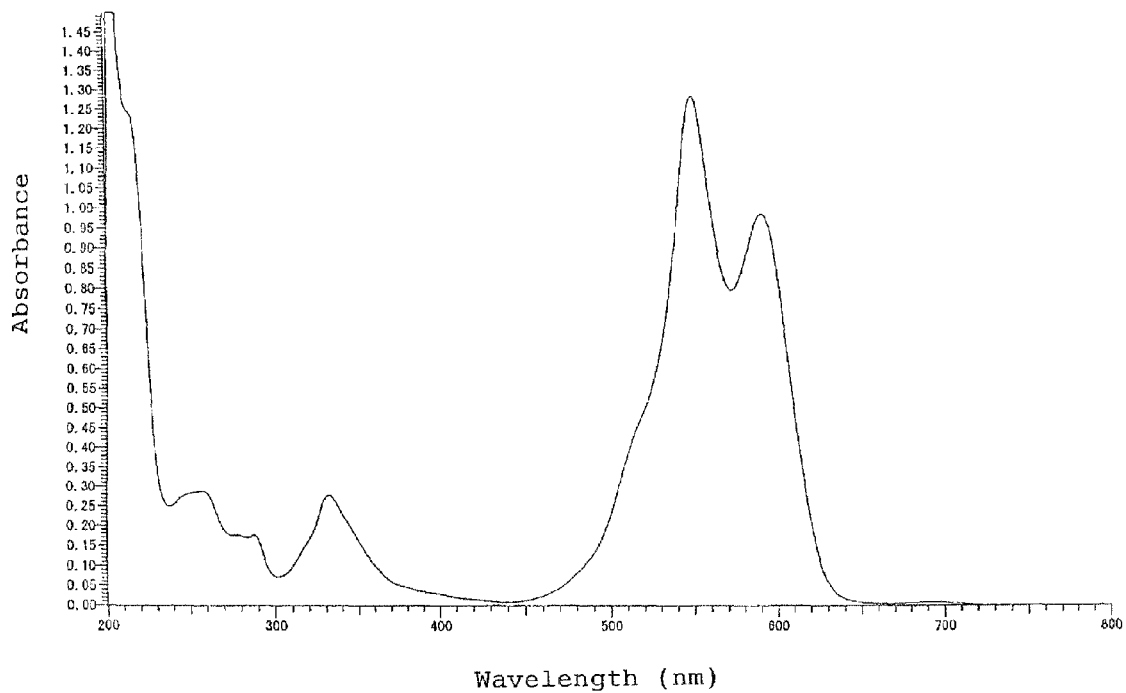

[FIG. 2]
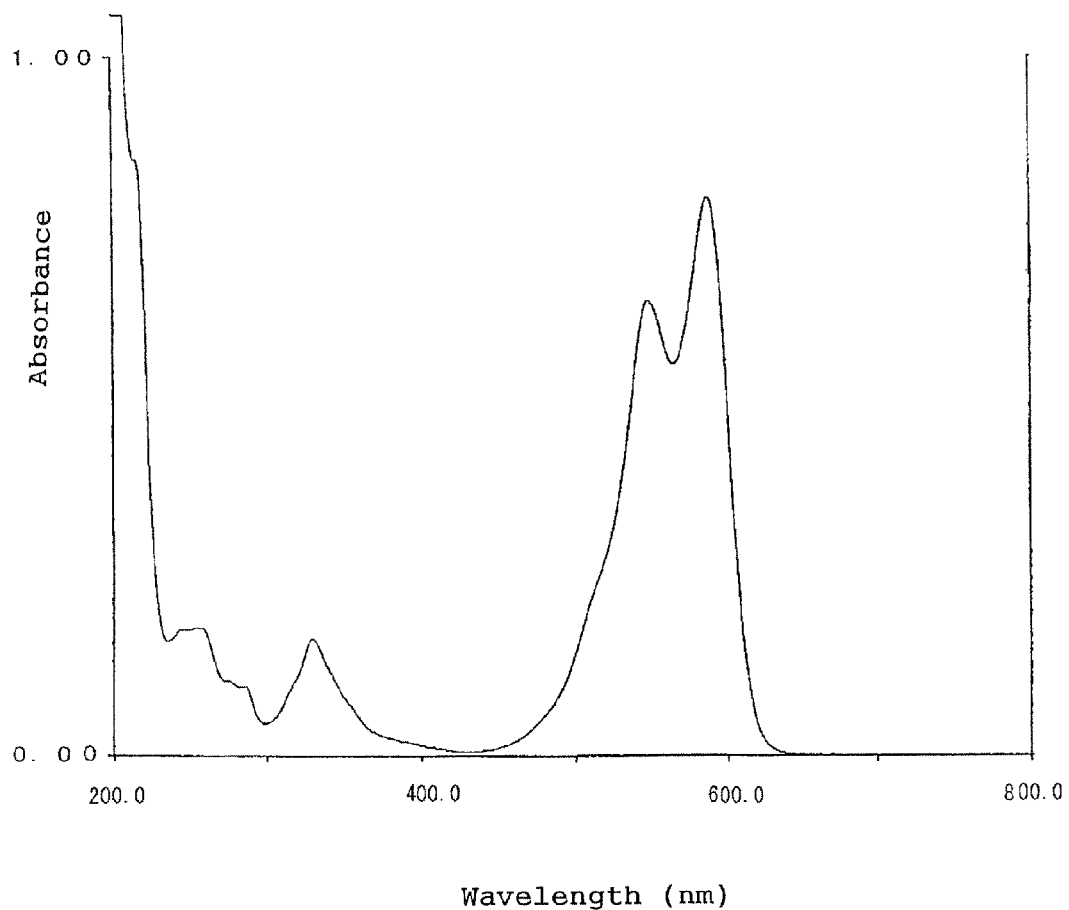

[FIG. 3]
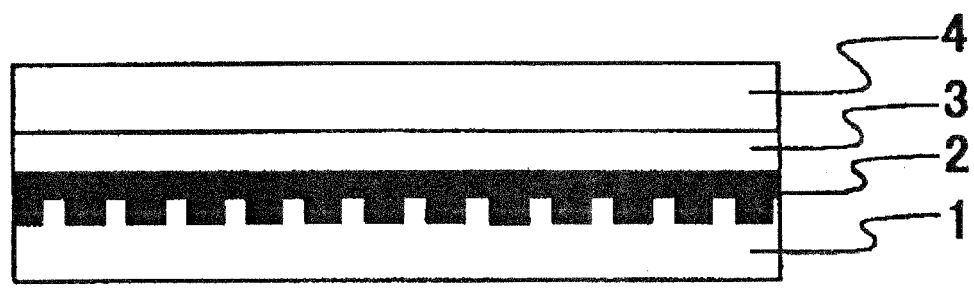

METHINE DYES AND USES OF THE SAME

TECHNICAL FIELD

The present invention relates to novel methine dyes and uses thereof, and more particularly, to methine dyes having a bis-indolenine skeleton composed of two indolenine rings linked together at their respective C-3 positions via a divalent linking group.

BACKGROUND ART

As coming into this information era, there has been in an increased demand for organic compounds capable of absorbing light in the ultra violet to the infrared regions. As can be seen in filter materials, the uses of such compounds have been expanded from the fields, where their properties of absorbing light to shield it are used, to others such as information recordings and solar energy generations, where light energy is positively used via the organic compounds.

The properties to be possessed by organic compounds applied to the above-identified fields can be listed as follows; a satisfactory light-absorption property and light tolerance in the ultra violet to the infrared regions, an improved solubility in solvents, and an exertion of thermal property depending on uses. Representative examples of organic compounds proposed so far include anthraquinone dyes phthalocyanine dyes, cyanine dyes as methane dyes, and styryl dyes (see, for example, Japanese Patent Kokai Nos. 116611/89, 2002-202592, 2003-167343, 58961/99, and 2003-231359), and among which anthraquinone dyes are said to be defective in light absorption property and phthalocyanine dyes are said to be defective in both light absorption property and solubility in solvents. Methine dyes have been tried to improve their light absorption property and solubility by the introduction of substituents and the dimerization of dye skeleton, however, even now there are only a few that fulfil functions such as light tolerance and thermal property, as well as light absorption property and solubility.

As coming into this multi-media age, optical recording media such as CD-Rs, DVD-Rs, recordable blue-laser disks (abbreviated as "BD-Rs", herein after), and HD DVD-Rs are highlighted in the field of information recordings. The optical recording media can be roughly classified into light-magnetic recording media, phase-change recording media, chalcogen oxide recording media, and organic optical recording media.

Among which, organic optical recording media are usually prepared by dissolving methine dyes in organic solvents such as 2,2,3,3-tetra fluoro-1-propanol (abbreviated as "TFP", herein after), applying the solutions over polycarbonate substrates, drying the resulting substrates to form recording layers, and sequentially attaching thereunto reflection layers of metals such as gold, silver, or copper and protection layers of ultra violet ray hardening resins. Organic optical recording media have the defects that the recording layers are susceptible to change due to environmental light such as reading light and natural light, but have the merits that they can be prepared at a lesser cost because recording layers can be formed by directly applying methine dyes, as light-absorption materials, in a solution form.

What is urgently required in organic optical recording media is to more increase their recording intensity and information-recording speed to meet this multi-media age. For such high density growth, it has been promoted to shorten the wavelength of light used for writing and reading. To attain a more increased high speed, more sensitive methine dyes should be desirably used, however, it tends to increase jitters to the time direction of reproduction signals and to lower light stability (light tolerance). To meet a further improvement in such high speed trend in the future, mere application of conventionally known methine dyes to such optical recording media is becoming to be incapable of attaining sufficient sensitivity, jitter, and light stability effective to record information at a relatively high speed.

DISCLOSURE OF INVENTION

In view of the foregoing, the present invention has an object to widen the applicability of organic compounds selectable as light-absorption materials in the above-identified uses by providing novel organic compounds which absorb light in the ultra violet and the infrared regions, have an improved light tolerance and solubility in solvents, and have thermal property corresponding to uses to which the organic compounds are applied.

Further the present invention has an object to provide optical recording media containing such organic compounds.

Still further the present invention has an object to provide intermediates useful for producing such organic compounds and methods for producing the organic compounds.

The present inventors energetically studied and screened methine dyes, which had been recognized to have poor light tolerance and thermal property, and revealed that the methine dyes, which have a bis-indolenine skeleton composed of two indolenine rings linked together at their respective C-3 positions via a divalent linking group, have an improved light tolerance, efficiently absorb light in the ultra violet and the infrared regions, exhibit solubility in various organic solvents without giving any actual hindrance, and have an improved thermal property. Thus, it was revealed that the methine dyes can be advantageously used in various uses which require the methine dyes with such properties to absorb light in the ultra violet and the infrared regions and to shield it, and used as novel light-absorption materials which use the energy of light in the ultra violet and the infrared regions.

The present inventors found that, when applied to optical recording media, the methine dyes exert the desired recording properties, as well as having a desired sensitivity and an improved light tolerance and jitter.

The present invention solves the above objects by providing the methine dyes having a bis-indolenine skeleton composed of two indolenine rings linked together at their respective C-3 positions via a divalent linking group.

Particularly, as a preferred embodiment, the present invention solves the above objects by providing the methine dyes containing the atomic groups represented by General Formula 1.

General Formula 1:

General Formula 1:

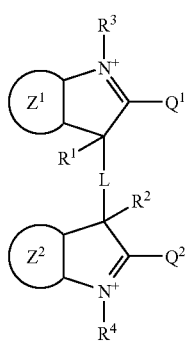

(In General Formula 1, $Z^1$ and $Z^2$ each independently represent aromatic rings which may have substituents. $R^1$ and $R^2$ each independently represent hydrogen atoms or appropriate substituents. $R^3$ and $R^4$ are the same or different hydrocarbon groups which may have substituents. L represents a divalent linking group which may have a substituent. $Q^1$ and $Q^2$ each independently represent monomethine or polymethine chains, having aromatic, heterocyclic, or amino groups at their opposite ends, which may have substituents and/or cyclic groups.)

Further, as a preferred embodiment, the present invention solves the above objects by providing methine dyes containing the atomic groups represented by General Formula 2.

General Formula 2:

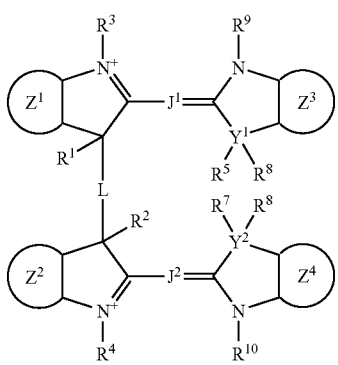

(In General Formula 2, $Z^1$ to $Z^4$ each independently represent aromatic rings which may have substituents. $R^1$, $R^2$, $R^5$, $R^6$, $R^7$ and $R^8$ each independently represent hydrogen atoms or appropriate substituents. $R^3$, $R^4$, $R^9$ and $R^{10}$ are the same or different hydrocarbon groups which may have substituents. Any two of the substituents for $R^5$ to $R^8$ or of the hydrocarbons for $R^9$ and $R^{10}$ may be linked together via a divalent linking group. L represents a divalent linking group which may have a substituent. $J^1$ and $J^2$ each independently represent monomethine or polymethine chains, which may have substituents and/or cyclic structures. $Y^1$ and $Y^2$ each independently represent carbon atoms or hetero atoms, and when $Y^1$ and/or $Y^2$ are hetero atoms, part or the whole of $R^5$ to $R^8$ do not exist.)

Further, the present invention solves the above objects by providing optical recording media containing the methine dyes.

Still further, the present invention solves the above objects by providing indolenine compounds represented by General Formula 3 as intermediates useful for producing the methine dyes.

General Formula 3:

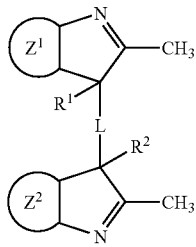

(In General Formula 3, $Z^1$ and $Z^2$ each independently represent aromatic rings which may have substituents. $R^1$ and $R^2$ each independently represent hydrogen atoms or appropriate substituents. L represents a divalent linking group which may have a substituent.)

Further, the present invention solves the above objects by providing processes for producing indolenine compounds, which contain a step of allowing any of the diketone compounds represented by General Formula 4 to react with one or two hydrazine compounds represented by General Formula 5.

General Formula 4:

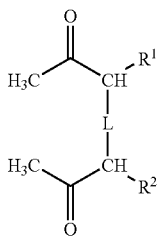

(In General Formula 4, L represents a divalent linking group, corresponding to L in General Formula 3, which may have a substituent.)

General Formula 5:

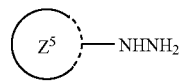

(In General Formula 5, $Z^5$ represents aromatic ring $Z^1$ or $Z^2$, corresponding to those in General Formula 3, which may have a substituent.)

The present invention was made based on both the creation of novel methine dyes, which substantially absorb light in the ultra violet and the infrared regions, and the finding of their industrially useful properties.

BRIEF EXPLANATION OF THE ACCOMPANYING DRAWINGS

FIG. 1 is an absorption spectrum of a trimethine dye in a solution form, among the methine dyes having a bis-indolenine skeleton of the present invention.

FIG. 2 is an absorption spectrum of a conventionally known trimethine dye, having a bis-indolenine skeleton, in a solution form.

FIG. 3 is a schematic view of an optical recording medium used in a specific Example.

EXPLANATION OF SYMBOLS

1 Substrate
2 Recording layer
3 Reflection layer
4 Protection layer

BEST MODE FOR CARRYING OUT THE INVENTION

As described above, the present invention relates to methine dyes having a bis-indolenine skeleton composed of two indolenine rings linked together at their respective C-3 positions via a divalent linking group.

The term "bis-indolenine skeleton" as referred to as in the present invention means the one composed of two indolenine rings that are linked together with a divalent linking group through carbon atoms at the C-3 positions of the two indolenine rings. The methine dyes of the present invention are novel compounds which are not disclosed in any previous literatures, and any methine dyes can be advantageously used in the present invention to some degree or another, as long as they contain a bis-indolenine skeleton composed of two indolenine rings linked together at their respective C-3 positions via a divalent linking group.

Examples of the methine dyes of the present invention include those which have a bis-indolenine skeleton that binds to one end of any one of the methine chains, for example, monomethine, dimethine chains, and other polymethine chains such as trimethine, tetramethine, pentamethine, hexamethine, heptamethine, and azamethine chains, which may have one or more substituents; and have an aromatic ring, heterocycle or amino group, which may have one or more substituents, binding to the other end of the methine chain.

Examples of the aromatic rings in the methine dyes include monocyclic or polycyclic aromatic rings with benzene ring as the basic unit; benzene, naphthalene, anthracene, phenanthrene rings, or the like. Examples of the heterocycles in the methine dyes include imidazoline ring, imidazole ring, benzimidazole ring, α-naphthoimidazole ring, β-naphthoimidazole ring, indole ring, isoindole ring, indolenine ring, isoindolenine ring, benzindolenine ring, pyridinoindolenine ring, oxazoline ring, oxazole ring, isoxazole ring, benzoxazole ring, pyridinooxazole ring, α-naphthoxazole ring, β-naphthoxazole ring, selenazoline ring, selenazole ring, benzoselenazole ring, α-naphthselenazole ring, β-naphthselenazole ring, thiazoline ring, thiazole ring, isothiazole ring, benzothiazole ring, α-naphthothiazole ring, β-naphthothiazole ring, tellulazoline ring, tellulazole ring, benzotellulazole ring, α-naphthotellulazole ring, β-naphthotellulazole ring, aquaridine ring, anthracene ring, isoquinoline ring, isopyrrole ring, imidaquinoxaline ring, indandione ring, indazole ring, indoline ring, oxadiazole ring, carbazole ring, xanthene ring, quinazoline ring, quinoxaline ring, quinoline ring, chroman ring, cyclohexanedione ring, cyclopentanedione ring, cinnoline ring, thiodiazole ring, thiooxazolidone ring, thiophene ring, thionaphthene ring, thiobarbituric acid ring, thiohydantoin ring, tetrazole ring, triazine ring, naphthalene ring, naphthyridine ring, piperazine ring, pyrazine ring, pyrazole ring, pyrazoline ring, pyrazolidine ring, pyrozolone ring, pyran ring, pyridine ring, pyridazine ring, pyrimidine ring, pyrylium ring, pyrrolidine ring, pyrroline ring, pyrrole ring, phenazine ring, phenanthridine ring, phenanthrene ring, phenanthroline ring, phthalazine ring, pteridine ring, furazan ring, furan ring, purine ring, benzoxazine ring, benzopyran ring, morpholine ring, and rhodanine ring. Examples of the amino groups in these methine dyes include phenylamino group, diphenylamino group, p-methoxyphenylamino group, methylamino group, dimethylamino group, ethylamino group, diethylamino group, or the like.

The methine dyes of the present invention are composed of the above-identified methine chains in combination with aromatic ring, heterocyclic ring or amino group, and concrete examples of such include dyes such as cyanine dyes, styryl dyes, merocyanine dyes, oxonol dyes, azulenium dyes, squallilium dyes, pyrilium dyes, thiopyrilium dyes, phenanthrene dyes, amino vinyl dyes, or the like.

Depending on use, particularly preferable methine dyes are, for example, those which contain the atomic groups represented by General Formula 1.

General Formula 1:

[Chem. 6]

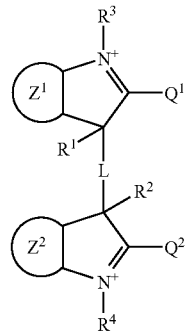

In General Formula 1, $Z^1$ and $Z^2$ each independently represent aromatic rings which may have a substituent. Examples of the aromatic rings for $Z^1$ and $Z^2$ include monocyclic or polycyclic aromatic rings with benzene ring as the base unit selected from benzene ring, naphthalene ring, anthracene ring, phenanthrene ring, and the like. These aromatic rings may have one or more substituents as long as they do not spoil the objects of the present invention. Examples of such substituents include aliphatic hydrocarbon groups such as methyl, ethyl, propyl, isopropyl, isopropenyl, 1-propenyl, 2-propenyl, 2-propynyl, butyl, isobutyl, sec-butyl, tert-butyl, 2-butenyl, 1,3-butadienyl, pentyl, isopentyl, neopentyl, tert-pentyl, 1-methylpentyl, 2-methylpentyl, and 2-pentene-4-ynyl groups; alicyclic hydrocarbon groups such as cyclopropyl, cyclobutyl, cyclopentyl, cyclohexyl, and cyclohexenyl groups; aromatic hydrocarbon groups such as phenyl, o-tolyl, m-tolyl, p-tolyl, xylyl, mesityl, o-cumenyl, m-cumenyl, p-cumenyl, and biphenylyl groups; ether groups such as methoxy, ethoxy, propoxy, isopropoxy, butoxy, isobutoxy, sec-butoxy, tert-butoxy, pentyloxy, and phenoxy groups; ester groups such as methoxycarbonyl, ethoxycarbonyl, propoxycarbonyl, acetoxy, and benzoyloxy groups; amino groups such as dimethylamino, diethylamino, dipropylamino, diisopropylamino, dibutylamino, and dipentylamino groups; halogen groups such as fluoro, chloro, bromo, and iodo groups; hydroxy group; carboxy group; cyano group; nitro group; and combinations thereof.

In General Formula 1, $R^1$ and $R^2$ each independently represent hydrogen atoms or appropriate substituents. Examples of such substituent include aliphatic hydrocarbon groups such as methyl, ethyl, propyl, isopropyl, isopropenyl, 1-propenyl, 2-propenyl, 2-propynyl, butyl, isobutyl, sec-butyl, tert-butyl, 2-butenyl, 1,3-butadienyl, pentyl, isopentyl, neopentyl, tert-pentyl, 1-methylpentyl, 2-methylpentyl, and 2-pentene-4-ynyl groups; alicyclic hydrocarbon groups such as cyclopropyl, cyclobutyl, cyclopentyl, cyclohexyl, and cyclohexenyl groups; aromatic hydrocarbon groups such as phenyl, o-tolyl, m-tolyl, p-tolyl, xylyl, mesityl, o-cumenyl, m-cumenyl, p-cumenyl, and biphenylyl groups; ether groups such as methoxy, ethoxy, propoxy, isopropoxy, butoxy, isobutoxy, sec-butoxy, tert-butoxy, pentyloxy, and phenoxy groups; ester groups such as methoxycarbonyl, ethoxycarbonyl, propoxycarbonyl, acetoxy, and benzoyloxy groups; amino groups such as dimethylamino, diethylamino, dipropylamino, diisopropylamino, dibutylamino, and dipentylamino groups; halogen groups such as fluoro, chloro, bromo, and iodo groups; hydroxy group; carboxy group; cyano group; nitro group; and combinations thereof.

In General Formula 1, $R^3$ and $R^4$ each independently represent the same or different hydrocarbon groups which may have substituents. Examples of such hydrocarbon groups include those which have carbon atoms of 1 to 20, usually, 1 to 8, such as methyl, ethyl, vinyl, ethyl, propyl, isopropyl, isopropenyl, 1-propenyl, 2-propenyl, 2-propynyl, butyl, isobutyl, sec-butyl, tert-butyl, 2-butenyl, 1,3-butadienyl, pentyl, isopentyl, neopentyl, tert-pentyl, 1-methylpentyl, 2-methylpentyl, and 2-pentene-4-ynyl, hexyl, isohexyl, 5-methylhexyl, heptyl, and octyl groups; wherein one or more of the hydrogen atoms of which may be substituted with aromatic hydrocarbon groups such as phenyl, o-tolyl, m-tolyl, p-tolyl, xylyl, mesityl, o-cumenyl, m-cumenyl, and p-cumenyl groups; ether groups such as methoxy, ethoxy, propoxy, isopropoxy, butoxy, isobutoxy, sec-butoxy, tert-butoxy, pentyloxy, phenoxy, and benzyloxy groups; halogen groups such as fluoro, chloro, bromo, and iodo groups; carboxy group; nitro group; and cyano group.

In General Formula 1, L represents a divalent linking group which may have a substituent. The term "divalent linking group" as referred to as in the present invention means a substituent having two linking sites for linking together the above-identified indolenine rings. Respective examples of the divalent linking group include aliphatic hydrocarbon groups such as methylene, ethylene, vinylene, trimethylene, propylene, propenylene, tetramethylene, penta methylene, hexamethylene, and octamethylene groups; alicyclic hydrocarbon groups such as cyclobutylene, cyclopentylene, cyclohexylene, cycloheptylene, cyclooctylene, cyclohexenylene, and cyclohexadienylene groups; aromatic hydrocarbon groups such as o-phenylene, m-phenylene, p-phenylene, diphenyl, naphthylene, 1,2-phenylenedimethylene, 1,3-phenylenedimethylene, 1,4-phenylenedimethylene, 1,4-phenylenediethylene, methylenediphenylene, and ethylenediphenylene groups; characteristic groups such as oxy and carbonyl groups which contain oxygen atom; ether groups such as methylenedioxy and ethylenedioxy groups; acyl groups such as oxalyl, malonyl, succinyl, glutaryl, adipoyl, suberoyl, o-phthaloyl, m-phthaloyl, and p-phthaloyl groups; characteristic groups such as thio and thiocarbonyl groups which contain sulfur atom; characteristic groups such as imino and azo groups which contain nitrogen atom; cycloalkylenedialkylene groups such as cyclopentylenedimethylene and cyclohexylenedimethylene groups; alkylenedicycloalkylene groups such as methylenedicyclohexylene and ethylenedicyclohexylene groups; and combinations thereof. Among which, considering both of the synthetic easiness and the solubility in solvents of methine dyes, preferable are those which have a chain length of the divalent linking group of less than 20, particularly, 1 to 10, and more particularly, 3 to 8, in terms of the number of constituent atoms such as carbon atoms. One or more of the hydrogen atoms of these divalent linking groups can be optionally substituted with amino group, carboxy group, cyano group, nitro group, halogen group, hydroxy group, or the like, as long as they do not spoil the scope of the present invention.

In General Formula 1, $Q^1$ and $Q^2$ each independently represent monomethine or polymethine chains with an aromatic ring, heterocycle, or amino group, which may have a substituent and/or cyclic group, at their respective opposite ends.

The aromatic rings in $Q^1$ and $Q^2$ can be selected from monocyclic or polycyclic rings with benzene ring as the basic unit, such as benzene, naphthalene, anthracene, and phenanthrene rings. These aromatic rings may have one or more substituents as long as they do not spoil the objects of the present invention. Respective examples of such include aliphatic hydrocarbon groups such as methyl, ethyl, propyl, isopropyl, isopropenyl, 1-propenyl, 2-propenyl, 2-propynyl, butyl, isobutyl, sec-butyl, tert-butyl, 2-butenyl, 1,3-butadienyl, pentyl, isopentyl, neopentyl, tert-pentyl, 1-methylpentyl, 2-methylpentyl, and 2-pentene-4-ynyl groups; alicyclic hydrocarbon groups such as cyclopropyl, cyclobutyl, cyclopentyl, cyclohexyl, and cyclohexenyl groups; aromatic hydrocarbon groups such as phenyl, o-tolyl, m-tolyl, p-tolyl, xylyl, mesityl, o-cumenyl, m-cumenyl, p-cumenyl, and biphenylyl groups; ether groups such as methoxy, ethoxy, propoxy, isopropoxy, butoxy, isobutoxy, sec-butoxy, tert-butoxy, pentyloxy, and phenoxy groups; ester groups such as methoxycarbonyl, ethoxycarbonyl, propoxycarbonyl, acetoxy, and benzoyloxy groups; amino groups such as dimethylamino, diethylamino, dipropylamino, diisopropylamino, dibutylamino, and dipentylamino groups; halogen groups such as fluoro, chloro, bromo, and iodo groups; hydroxy group; carboxy group; cyano group; nitro group; and combinations thereof.

Examples of the heterocycles in $Q^1$ and $Q^2$ include the following monocyclic or polycyclic ones which contain one or more hetero atoms selected from the 15 or 16 group in the periodic law table such as nitrogen, oxygen, sulfur, selenium, and tellurium atoms; imidazoline ring, imidazole ring, benzimidazole ring, α-naphthoimidazole ring, β-naphthoimidazole ring, indole ring, isoindole ring, indolenine ring, isoindolenine ring, benzindolenine ring, pyridinoindolenine ring, oxazoline ring, oxazole ring, isoxazole ring, benzoxazole ring, pyridinooxazole ring, α-naphthoxazole ring, β-naphthoxazole ring, selenazoline ring, selenazole ring, benzoselenazole ring, α-naphthselenazole ring, β-naphthselenazole ring, thiazoline ring, thiazole ring, isothiazole ring, benzothiazole ring, α-naphthothizole ring, β-naphthothizole ring, tellulazoline ring, tellulazole ring, benzotellulazole ring, α-naphthotellulazole ring, β-naphthotellulazole ring, aquaridine ring, anthracene ring, isoquinoline ring, isopyrrole ring, imidaquinoxaline ring, indandione ring, indazole ring, indoline ring, oxadiazole ring, carbazole ring, xanthene ring, quinazoline ring, quinoxaline ring, quinoline ring, chroman ring, cyclohexanedione ring, cyclopentanedione ring, cinnoline ring, thiodiazole ring, thiooxazolidone ring, thiophene ring, thionaphthene ring, thiobarbituric acid ring, thiohydantoin ring, tetrazole ring, triazine ring, naphthalene ring, naphthyridine ring, piperazine ring, pyrazine ring, pyrazole ring, pyrazoline ring, pyrazolidine ring, pyrazolone ring, pyran ring, pyridine ring, pyridazine ring, pyrimidine ring, pyrylium ring, pyrrolidine ring, pyrroline ring, pyrrole ring, phenazine ring, phenanthridine ring, phenanthrene ring, phenanthroline ring, phthalazine ring, pteridine ring, furazan ring, furan ring, purine ring, benzoxazine ring, benzopyran ring, morpholine ring, and rhodanine ring. These heterocycles may have one or more substituents as long as they do not spoil the object of the present invention, and respective examples of such are the same substituents as those in the above-mentioned aromatic rings.

Examples of the amino groups in $Q^1$ and $Q^2$ include phenylamino, diphenylamino, p-methoxyphenylamino, methylamino, dimethylamino, ethylamino, diethylamino, or the like.

The polymethine chains in $Q^1$ and $Q^2$ can be selected from, for example, polymethine chains with an odd number of methine groups successively linked together, such as trimethine, pentamethine, and heptamethine groups; polymethine chains with an even number of methine groups successively linked together, such as dimethine, tetramethine, and hexamethine groups; and polymethine chains such as azamethine chain. The monomethine or polymethine chain may have a substituent and/or a cyclic group, and examples of such substituent include aliphatic hydrocarbon groups such as methyl, trifluoromethyl, ethyl, propyl, isopropyl, butyl, isobutyl, sec-butyl, tert-butyl, pentyl, isopentyl, neopentyl, and tert-pentyl; ether groups such as methoxy, trifluoromethoxy, ethoxy, propoxy, butoxy, and tert-butoxy; halogen groups such as fluoro, chloro, bromo, and iodo groups; amino groups such as diphenylamino and p-methoxydiphenylamino groups; nitro group; and cyano group. Examples of the cyclic groups include cyclopentene, cyclopentadiene, cyclohexene, cyclohexadiene, cycloheptene, cyclooctene, cyclooctadiene, and benzene rings.

More preferred examples of the methine dyes include those which have the atomic groups represented by General Formula 2.

General Formula 2:

[Chem. 7]

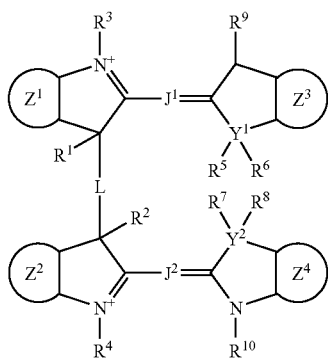

In General Formula 2, $Z^1$ to $Z^4$ each independently represent aromatic rings which may have substituents. Examples of the substituents include monocyclic or polycyclic rings with benzene ring as the basic unit, selected from benzene, naphthalene, anthracene, and phenanthrene rings. These aromatic rings may have one or more substituents as long as they do not spoil the objects of the present invention, and respective examples of such substituents include the same ones as those in General Formula 1.

$Y^1$ and $Y^2$ in General Formula 2 represent carbon atoms or hetero atoms, and examples of such hetero atoms include those selected from the 15 or 16 group in the periodic law table such as nitrogen, oxygen, sulfur, selenium, and tellurium atoms. The carbon atoms in $Y^1$ and $Y^2$ can be, for example, atomic groups such as ethylene and vinylene groups including two carbon atoms mainly. $Y^1$ and $Y^2$ in General Formula 1 can be the same or different each other.

$R^1$, $R^2$ and $R^5$ to $R^8$ in General Formula 2 each independently represent hydrogen atoms or appropriate substituents. Examples of the substituents for $R^1$, $R^2$ and $R^5$ to $R^8$ include, for example, the same ones as those for $R^1$ and $R^2$ in General Formula 1. When $Y^1$ and/or $Y^2$ is/are a hetero atom(s), part or the whole of $R^5$ to $R^8$ does/do not apparently exist.

$R^3$, $R^4$, $R^9$ and $R^{10}$ in General Formula 2 each independently represent the same or different hydrocarbon groups which may have a substituent. Examples of the hydrocarbon groups for $R^3$, $R^2$, $R^9$ and $R^{10}$ include the same ones as those in $R^3$ and $R^4$ in General Formula 1.

Any two of the substituents in $R^5$ to $R^8$ or the hydrocarbon groups in $R^9$ and $R^{10}$ can be linked together via any one of the following divalent linking groups: Aliphatic hydrocarbon groups such as methylene, ethylene, vinylene, trimethylene, propylene, propenylene, tetramethylene, pentamethylene, hexamethylene, and octamethylene; alicyclic hydrocarbon groups such as cyclobutylene, cyclopentylene, cyclohexylene, cycloheptylene, cyclooctylene, cyclohexenylene, and cyclohexadienylene; aromatic hydrocarbon groups such as o-phenylene, m-phenylene, p-phenylene, diphenylene, naphthylene, 1,2-phenylenedimethylene, 1,3-phenylenedimethylene, 1,4-phenylenedimethylene, 1,4-phenylenediethylene, methylenediphenylene, and ethylenediphenylene; characteristic groups such as oxy and carbonyl groups which contain oxygen atom; ether groups such as methylenedioxy and ethylenedioxy groups; acyl groups such as oxalyl, malonyl, succinyl, glutaryl, adipoyl, suberoyl, o-phthaloyl, m-phthaloyl, and p-phthaloyl groups; characteristic groups such as thio and thiocarbonyl groups which contain sulfur atom; characteristic groups such as imino and azo groups which contain nitrogen atom; cycloalkylenedialkylene groups such as cyclopentylenedimethylene and cyclohexylenedimethylene groups; alkylenedicycloalkylene groups such as methylenedicyclohexylene and ethylenedicyclohexylene groups; and combinations thereof.

L in General Formula 2 represents a divalent linking group, which corresponds to L in General Formula 1 and which may have a substituent. Respective examples of the divalent linking group can be listed as the same ones as those in General Formula 1.

$J^1$ and $J^2$ in General Formula 2 represent monomethine or polymethine chains. Respective examples of the polymethine chains can be selected from polymethine chains with an odd number of methine groups successively linked together, such as trimethine, pentamethine, and heptamethine groups; and polymethine chains with an even number of methine groups successively linked together, such as dimethine, tetramethine, and hexamethine groups. These monomethine or polymethine groups may have substituents and/or cyclic groups.

Examples of the monomethine or polymethine groups include, for example, aliphatic hydrocarbon groups such as methyl, trifluoromethyl, ethyl, propyl, isopropyl, butyl, isobutyl, sec-butyl, tert-butyl, pentyl, isopentyl, neopentyl, and tert-pentyl; ether groups such as methoxy, trifluoromethoxy, ethoxy, propoxy, butoxy, and tert-butoxy; alicyclic hydrocarbon groups such as cyclopropyl, cyclobutyl, cyclopentyl, cyclopentenyl, cyclohexyl, and cyclohexenyl groups; aromatic hydrocarbon groups such as phenyl and naphthyl groups; halogen groups such as fluoro, chloro, bromo, and iodo groups; amino groups such as diphenylamino and p-methoxydiphenylamino groups; heterocyclic groups such as piperidino and morpholino groups; nitro group; cyano group; and combinations thereof. Examples of the cyclic structures of the polymethine groups include, for example, cyclopentene, cyclopentadiene, cyclohexene, cyclohexadiene, cycloheptene, cyclooctene, cyclooctadiene, and benzene rings, which contain, for example, at least one unsaturated bond such as ethylene double bond that electronically resonates as a part of polymethine chain, and any of which may have substituents similar to those in the above-identified polymethine chains.

In the case that the methine dyes of the present invention require counter ions, such counter ions can be determined to be appropriate ones, while considering the solubility of the methine dyes in organic solvents and their stability in glassy state, and usually, the counter ions can be selected from inorganic acid anions such as fluoric, chloric, bromic, iodic, perchloric, periodic, phosphoric acid hexa fluoride, antimony hexa fluoride, tin acid hexa fluoride, nitric acid, phosphoric acid, fluoroboric acid, and tetra fluoroborate ions; organic acid anions such as salicylic acid, p-hydroxy salicylic acid, thiocyanic acid, benzenesulfonic acid, naphthalenesulfonic acid, naphthalenedisulfonic acid, p-toluenesulfonic acid, alkylsulfonic acid, benzenesulfonic acid, alkylcarboxylic acid, trihaloalkylcarboxylic acid, alkylsulfonic acid, trihaloalkylsulfonic acid, and nicotinic acid ions; organic metal complex anions such as those of azo, bisphenyldithiol, thiocatecholchelate, thiobisphenolatechelate, bisdiol-α-diketone; and bisalkylsulfonylimides such as bistrifluoromethylsulfonylimide and pentafluoroethylsulfonylimide.

In the methine dyes represented by General Formulae 1 and 2, if they have structural isomers such as cis/trans isomers and enantiomers, any of such isomers should be included in the present invention.

Any of the methine dyes of the present invention have characteristic main absorption maxima in the ultra violet region to the infrared region, particularly, in the region at wavelengths of longer than 300 nm, more particularly, at wavelengths of around 350 to 850 nm, have distinctly high molecular absorption coefficients (may be abbreviated as "ε") of $1.0 \times 10^5$ or more, usually, $1.5 \times 10^5$ or more at their absorption maxima, and have higher decomposition points and improved thermostability. Thus, these methine dye compounds can be quite advantageously used in high-density optical recording media with a recording capacity of 15 to 23.3 GB per side, which use laser beams with wavelengths of about 405 nm as a recording light, such as BD-Rs and HD DVD-Rs, and optical recording media such as DVD-Rs using laser beams with wavelengths of 635 to 660 nm and CD-Rs using laser beams with wavelengths of about 780 nm.

Among the methine dyes with a bis-indolenine skeleton according to the present invention, the trimethine dye represented by Chemical Formula 2 exhibits a visible ray absorption spectrum in FIG. 1, when in a solution form. As shown in the visible absorption spectrum in FIG. 1, the trimethine dye has absorption maxima at respective wavelengths of about 550 nm and about 600 nm and substantially absorbs a recording light with a wavelength of around 635 to 660 nm at the longer wavelength side of the above each absorption maximum. While the conventionally known trimethine dye represented by Chemical Formula 67 with a bis-indolenine skeleton exhibits a visible absorption spectrum in FIG. 2, when in a solution form. Comparing these trimethine dyes, there found is a difference in their absorption wave-forms. It can be estimated that, comparing the conventionally known trimethine dye with a bis-indolenine skeleton bound together at their nitrogen atoms in the indolenine rings via a divalent linking group, the trimethine dye of the present invention, where a bis-indolenine skeleton is formed by indolenine rings bound together at their respective C-3 positions in each indolenine rings via a divalent linking group, easily forms H association product as a dimmer of methine dye. Accordingly, the absorption maxima of the methine dyes of the present invention will shift to the sides with slightly shorter wavelengths.

Concrete examples of the methine dyes of the present invention include, for example, those represented by Chemical Formulae 1 to 45.

Chemical Formula 1:

[Chem. 8]

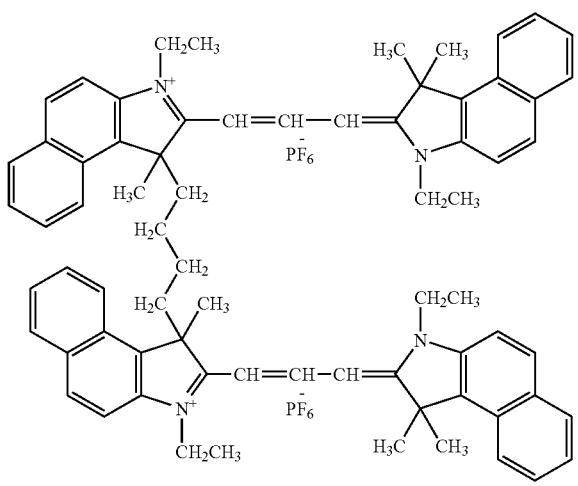

Chemical Formula 2:

-continued
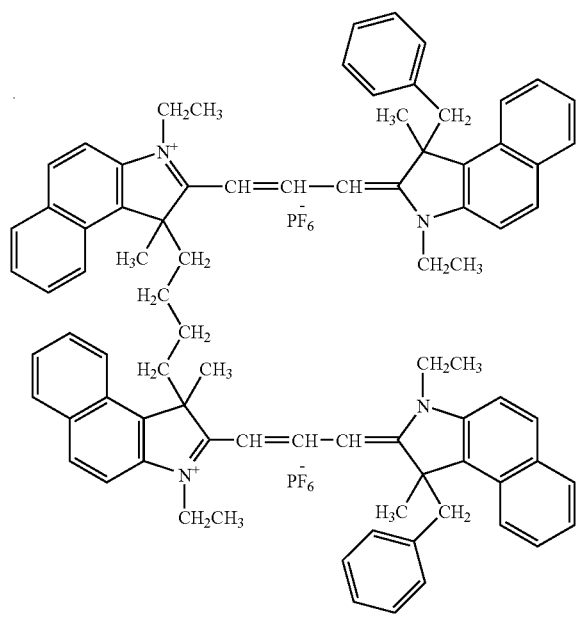
Chemical Formula 3:
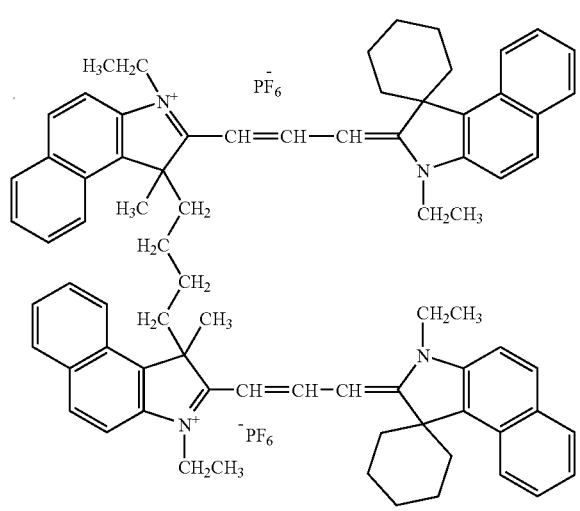
Chemical Formula 4:
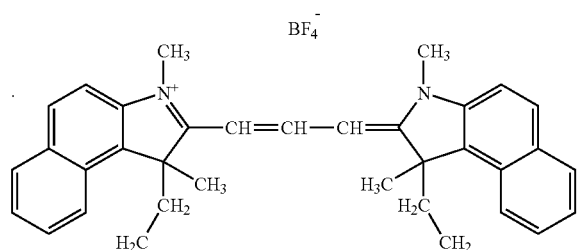

The methine dyes of the present invention can be synthesized by various methods, however, from an economical viewpoint, preferable are the methods which use nucleophilic displacement reaction of an active methine group and an appropriate elimination group. In the case of synthesizing the methine dyes with the atomic groups represented by General Formula 1 by using the above preferable methods, the methine dyes of the present invention can be obtained in a desired amount by either allowing the compounds represented by General Formula 6, which have $Z^1$, $Z^2$, $R^1$ to $R^4$, and L, corresponding to those in General Formula 1, to react with aromatic or heterocyclic compounds having appropriate elimination groups derived from $Q^1$ and/or $Q^2$; or allowing the compounds represented by General Formula 7, which have $Z^1$, $Z^2$, $R^1$ to $R^4$, and L, corresponding to those in General Formula 1, to react with aromatic or heterocyclic compounds having appropriate elimination groups derived from $Q^1$ and/or $Q^2$ General Formula 6:

[Chem. 53]

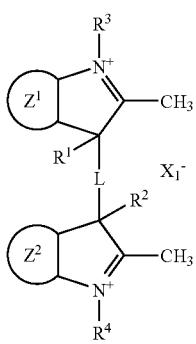

General Formula 7:

[Chem. 54]

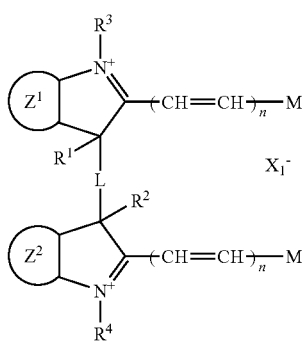

In the case of synthesizing the methine dyes with the atomic groups represented by General Formula 2 by using the above methods, the methine dyes of the present invention can be obtained in a desired amount by either allowing the compounds, having the atomic groups represented by General Formula 6, to react with the compounds represented by General Formula 8, which have $Z^3$, $R^5$, $R^6$, $R^9$ and $Y^1$, corresponding to those in General Formula 2, and/or the compounds having the atomic groups represented by General Formula 9, which have $Z^4$, $R^7$, $R^8$, $R^{10}$ and $Y^2$, corresponding to those in General Formula 2; or allowing the compounds having the atomic groups represented by General Formula 7 to react with the compounds represented by General Formula 10, which have $Z^3$, $R^5$, $R^6$, $R^9$ and $Y^1$, corresponding to those in General Formula 2, and/or the compounds represented by General Formula 11, which have $Z^4$, $R^7$, $R^8$, $R^{10}$ and $Y^2$, corresponding to those in General Formula 2. $X_1^-$ and $X_2^-$ in General Formulae 6 to 11 represent appropriate anions, for example, inorganic acid ions such as fluoric, chloric, bromic, iodic, perchloric, periodic, bromic acid, iodic acid, perchloric acid, periodic acid, phosphoric acid hexa fluoride, antimony hexa fluoride, tin acid hexa fluoride, fluoroboric acid, and tetra fluoroborate ions; organic acid ions such as thiocyanic acid, benzenesulfonic acid, naphthalenesulfonic acid, naphthalenedisulfonic acid, benzenecarboxylic acid, alkylcarboxylic acid, trihaloalkylcarboxylic acid, alkylsulfonic acid, trihaloalkylsulfonic acid, nicotinic acid, and tetracyanoquinonedimethane ions; and bisalkylsulfonylimide ions such as bistrifluoromethylsulfonylimide and pentafluoroethylsulfonylimide.

M in General Formulae 7 to 9 represents an appropriate elimination group and usually selected from monovalent groups of aniline or derivatives thereof such as anilino, p-toluidino, p-methoxyanilino, p-ethoxycarbonylanilino, N-acetylanilino groups; or sulfur-atom-containing characteristic groups such as mercapto, methylthio, ethylthio, 3-sulfonylpropyl, and 4-sulfonylbutyl groups. The symbol "n" represents an integer of 0 to 3.

General Formula 8:

[Chem. 55]

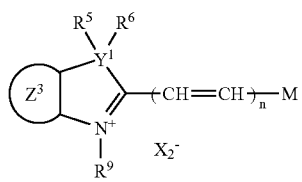

General Formula 9:

[Chem. 56]

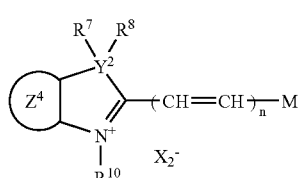

General Formula 10:

[Chem. 57]

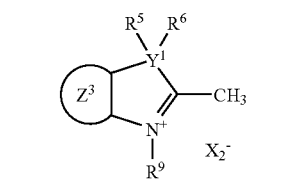

General Formula 11:

[Chem. 58]

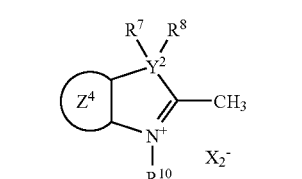

In synthesizing the methine dyes of the present invention, appropriate amounts of the compounds represented by General Formula 6 and the compounds represented by General Formula 8 and/or General Formula 9; or of the compounds represented by General Formula 7 and the compounds represented by General Formula 10 and/or General Formula 11 are placed in reaction vessels, and, if necessary, dissolved in appropriate solvents and admixed with, for example, basic compounds such as sodium hydroxide, potassium hydroxide, sodium carbonate, potassium carbonate, sodium hydrogencarbonate, potassium hydrogencarbonate, ammonia, triethylamine, piperidine, pyridine, pyrrolidine, aniline, N, N-dimethylaniline, and N, N-diethylaniline; acid compounds such as hydrochloric acid, sulfuric acid, nitric acid, acetic acid, trifluoroacetate, p-toluene sulfonate, methane sulfonate, and trifluoromethane sulfonate; Lewis acid compounds such aluminum chloride, zinc chloride, tin chloride, and titanium tetrachloride; and then the resulting mixtures are reacted at ambient temperature or over, under heating and stirring conditions, while heat refluxing.

Examples of such appropriate solvents include hydrocarbons such as pentane, hexane, cyclohexane, octane, benzene, toluene, and xylene; halogen compounds such as carbon tetrachloride, chloroform, 1,2-dichlorobenzene, 1,2-dibromobenzene, trichloroethylene, tetrachloroethylene, chlorobenzene, bromobenzene, and α-dichlorobenzene; alcohols and phenols such as methanol, ethanol, 1-propanol, 2-propanol, 1-butanol, 2-butanol, isobutyl alcohol, isopentyl alcohol, cyclohexanol, ethylene glycol, propylene glycol, 2-methoxyethanol, 2-ethoxyethanol, phenol, benzyl alcohol, cresol, diethylene glycol, triethylene glycol, and glycerine; ethers such as diethyl ether, diisopropyl ether, tetrahydrofuran, tetrahydropyran, 1,4-dioxane, anisole, 1,2-dimethoxyethane, diethylene glycol dimethyl ether, and dicyclohexyl-18-crown-6; acids and derivatives thereof such as acetic acid, acetic anhydride, trichloroacetate, trifluoroacetate, propionic acid anhydride, ethyl acetate, butyl carbonate, ethylene carbonate, propylene carbonate, formamide, N-methylformamide, N, N-dimethylformamide, N-methylacetamide, N, N-dimethylacetamide, and hexamethylphosphoric triamide; nitriles such as acetonitrile, propionitrile, succinonitrile, and benzonitrile; nitro compounds such as nitromethane and nitrobenzene; sulfur-atom-containing compounds such as dimethylsulfoxide and sulfolane; and water. Depending on use, these solvents can be used in an appropriate combination.

In the case of using the above solvents, the more the amount of the solvents used, the lower the reaction efficiency becomes, while the lower the amount of the solvents used, the more the homogeneous heating and stirring of the reaction mixtures becomes difficult or the more the formation of by-products tends to easily occur. Because of this, the amount of the solvents is preferably set to 100 times or lower, usually, 5 to 50 times by weight of the total amount of the material compounds used. Varying depending on the kind of the material compounds and the reaction conditions used, the reaction should preferably be completed within 10 hours, usually, 0.5 to 5 hours. The reaction procedure can be monitored, for example, by conventional methods such as thin layer chromatography, gas chromatography, and high performance liquid chromatography. The methine dyes of the present invention are produced in a desired amount by the above method or in accordance therewith. The reaction procedure can be monitored, for example, by conventional methods such as thin layer chromatography, gas chromatography, and high performance liquid chromatography.

The compounds represented by General Formulae 6 and 7 can be obtained through the compounds represented by General Formula 3 according to the present invention, for example, in accordance with the method disclosed in "Kanko-So" (Photosensitizing dyes), edited by Masaaki HAYAMI, published by Sangyo-Tosho Publisher, Tokyo Japan, pp. 24-30, Oct. 17, 1997. Similarly, the compounds represented by General Formulae 8, 9, 10 and 11 can be obtained in accordance with the method disclosed in "Kanko-So" (Photosensitizing dyes), edited by Masaaki HAYAMI, published by Sangyo-Tosho Publisher, Tokyo Japan, pp. 24-30, Oct. 17, 1997.

General Formula 3:

[Chem. 59]

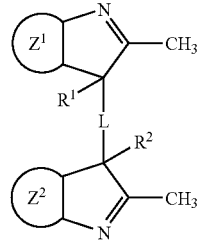

The indolenine compounds represented by General Formula 3 according to the present invention can be obtained through a step of reacting the diketone compounds represented by General Formula 4 with one or more hydrazine compounds represented by General Formula 5.

General Formula 4:

[Chem. 60]

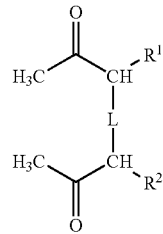

General Formula 5:

[Chem. 61]

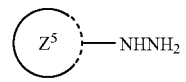

In the indolenine compounds represented by General Formula 3, if they have structural isomers such as enantiomers, any of such isomers should be included in the present invention.

Concrete examples of the indolenine compounds of the present invention include, for example, those represented by General Formulae 46 to 53. Any of which functions as intermediates for preparing the methine dyes of the present invention.

Chemical Formula 46:

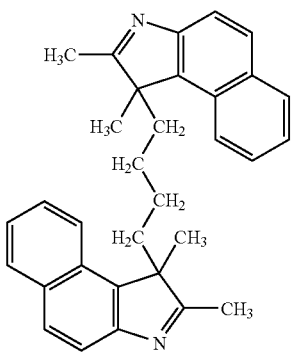
Chemical Formula 47:
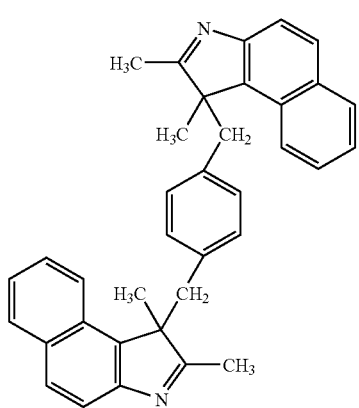
Chemical Formula 48:
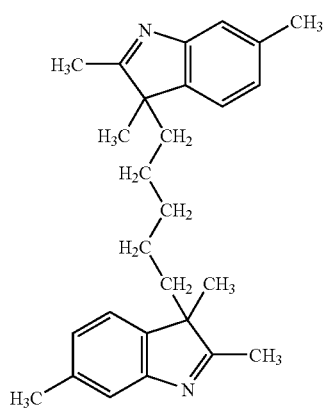
Chemical Formula 49:
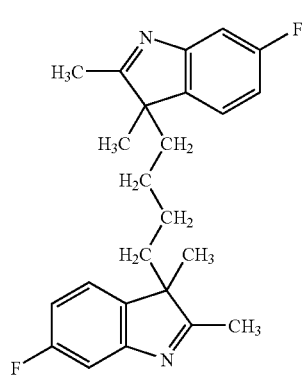
[Chem. 62] Chemical Formula 50:
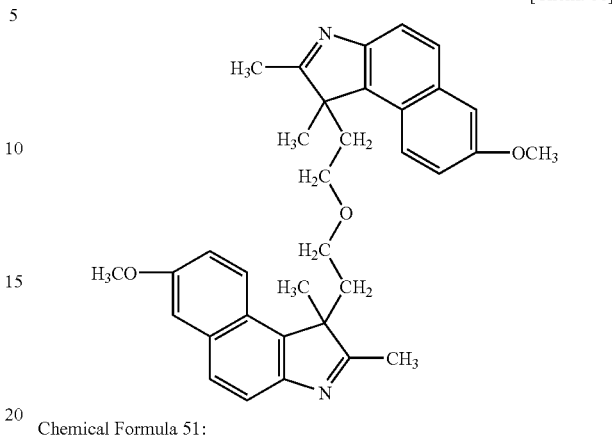
[Chem. 63]
Chemical Formula 51:
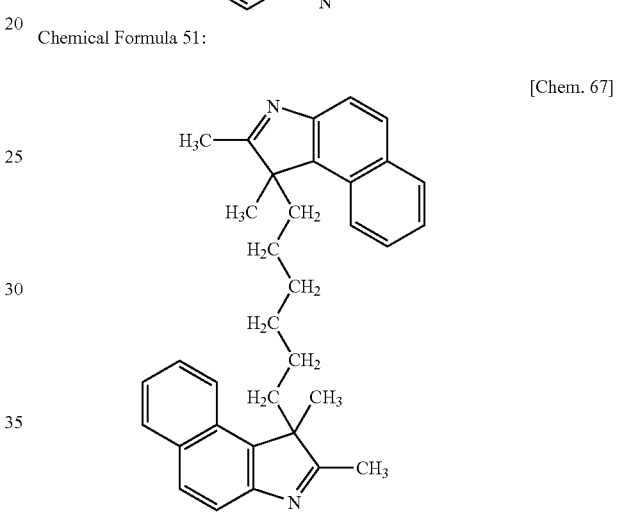
[Chem. 64]
Chemical Formula 52:
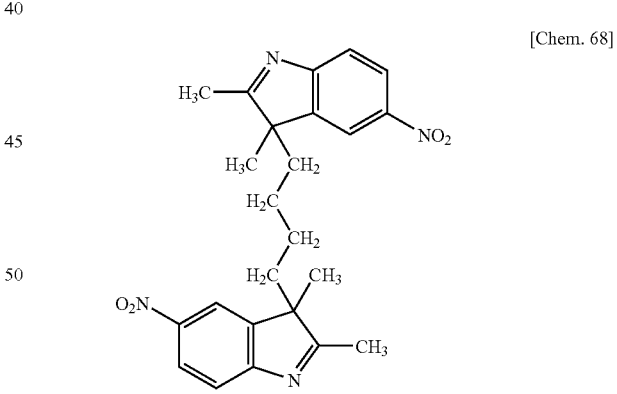
[Chem. 65]
Chemical Formula 53:

[Chem. 69]

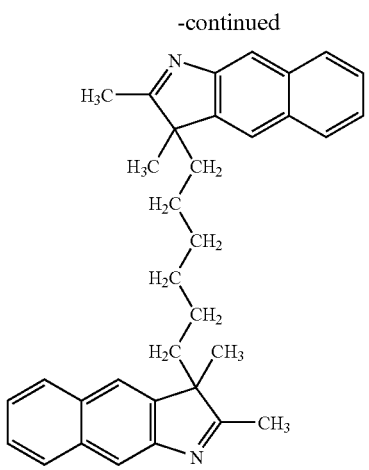

In synthesizing the above indolenine compounds, appropriate amounts of the respective compounds represented by General Formulae 4 and 5 are placed in a reaction vessel, and, if necessary, dissolved in an appropriate solvent and admixed with, for example, a basic compound such as sodium acetate, potassium acetate, potassium carbonate, calcium carbonate, triethylamine, N, N-dimethylaniline, piperidine, morpholine, pyridine, or 1,8-diazabicyclo[5.4.0]-7-undecene; and then the resulting mixture is reacted at ambient temperature or over under heating and stirring conditions, while heat refluxing. Examples of the solvents usable in the above include similar solvents to those used in synthesizing the methine dyes of the present invention. Varying depending on the kind of the material compounds and the reaction conditions used, the reaction should preferably be completed within 10 hours, usually, within five hours. The reaction procedure can be monitored, for example, by conventional methods such as thin layer chromatography, gas chromatography, and high performance liquid chromatography.

Depending on use, the methine dyes and the indolenine compounds thus obtained can be used intact in a reaction mixture form, and usually they can be used after purified by the methods generally used for purifying the related compounds thereof, such as dissolution, separation, decantation, filtration, extraction, concentration, thin-layer chromatography, column chromatography, gas chromatography, high performance liquid chromatography, distillation, sublimation, and crystallization; and, if necessary, these methods can be used in combination. Depending on the kinds and uses of the methine dyes and the indolenine compounds, when applied to, for example, information recording and solar energy generation which require relatively-high purity organic compounds, the methine dyes and the indolenine compounds should preferably be purified by the methods such as distillation, sublimation, and crystallization, prior to use.

As described above, the methine dyes of the present invention have main absorption maxima in the region at wavelengths of longer than 300 nm, usually, at wavelengths of around 350 to 850 nm, and have distinctly high molecular absorption coefficients (may be abbreviated as "$\epsilon$") of $1.0\times 10^5$ or more, usually, $1.5\times 10^5$ or more at their absorption maxima, and efficiently absorb the light in such wavelength region. The methine dyes of the present invention exhibit satisfactory solubility with no actual problem in organic solvents such as of amides, alcohols, ketones, nitriles, and halogens, which are frequently used, for example, in the fields of information recording and solar energy generation; and most of the methine dyes have decomposition points of about 200° C. or higher. As is well known, it is said that the decomposition point and the glass transition point of an organic compound are recognized as important indexes of their thermal stability, i.e., compounds with higher decomposition points and glass transition points tend to have a higher thermal stability. Accordingly, the methine dyes of the present invention can be quite advantageously used as light-absorption materials which absorb the light in the ultra violet and the infrared regions to shield it, or use the light energy of the above regions in various fields of, for example, information recordings, solar energy generations, electric equipments, electric communications apparatuses, optical equipments, clothes, building/bedding/decorating products, health goods, and agricultural materials. The decomposition points of the methine dyes can be determined by conventional differential thermogravimetry (abbreviated as "DSC" herein after).

When used in information recordings, the methine dyes of the present invention can be advantageously used as photosensitizers or heat-exchangers to promote polymerization by absorbing the light in the ultra violet and the infrared regions to sensitize polymerizable compounds and polymerization initiators used in optical cards, photoengravings, thermal transfer recordings, thermal recordings, hologram recordings, or the like. Referring to other uses as photosensitizers, for example, when applied to semiconductor electrodes for dye-sensitizing-wet-type solar cells in the field of solar energy generation, the methine dyes of the present invention augment the sensitivity of semiconductor electrodes to the visible light with shorter wavelengths and distinctly improve the light conversion efficiency of solar cells. Since the methine dyes of the present invention exert the desired light tolerance with no actual problem against environmental light such as natural and artificial light, the solar cells using the methine dyes as photosensitizers have the actual merit that they do not cause reduction of electromotive force inducible by the photosensitizers used, even when used for a relatively long period of time.

When used in the fields of electric communication apparatuses, electric equipments, and optical equipments, the methine dyes of the present invention can be applied as filter materials to pickup tubes, semiconductor light receiving elements, optical fibers, front panel materials for image-displaying apparatuses, or the like to exert the actual merits that they inhibit noises inherent to the light in the ultra violet and the infrared regions, inhibit the increment of ambient temperature caused by the emitted heat rays, and control the visibility to the desired level. Examples for other uses as filter materials, the methine dyes of the present invention can be used in agricultural materials, for example, in such a manner of being applied over glass plates for green houses and plastic bases for vinyl plastic hothouses shaped in a sheet or film form to control plant growth by regulating the wavelength distribution of light shed to fruit trees, crops, vegetables, decorative plants including flowering plants, garden plants, edible plants, and beneficial plants including medicinal plants.

In addition to the above uses, in combination with one or more other materials which absorb the light in the ultra violet, the visible and/or the infrared regions, the methine dyes of the present invention can be used as light-shielding agents, heat-ray-shielding-agents, heat-shielding agents, or agents for thermal insulation/storage in clothes in general, particularly, those which use thermal insulation/storage fibers and fibers capable of camouflaging against reconnaissance by ultraviolet ray, visible light, or infrared ray; and the followings other than clothes, for example, interior/exterior finish for a casement, shirring, drape, pleat, print, venetian blind, lace, Roman Shede, roll screen, shutter, shop curtain, blanket, thick bedquilt including comforter, peripheral material for the thick bedquilt, cover for the thick bedquilt, bed sheet, Japanese cushion, pillow, pillow cover, cushion, mat, carpet, sleeping bag, window glass including car window glass, building, vehicle, electric train, ship, and aircraft; building/bedding/decorating products such as a window glass; sanitary and health goods such as a paper diaper, diaper cover, eyeglasses, monocle, and lorgnette; internal base sheets; linings, internal and base materials for shoes; wrappers; materials for umbrellas; parasols; stuffed toys; lighting devices; sunglasses; sun visors; sunroofs; peeping windows of ovens including electric ones; and materials for wrapping and injecting or containers to wrap, inject or enclose the above-identified products, whereby the methine dyes of the present invention prevent or reduce the disorders and inconveniences of the above products and living bodies such as the undesired change in temperature, asthenopia induced by the visible light, aging of photoreceptor cells, and cataract; modify the color, color tone, color tint, and color appearance; and maintain and control the light reflected from or passed through the above products to the desired levels. Similarly as conventionally known organic compounds which absorb the visible light, the methine dyes of the present invention are useful in indelible inks, indelible/forgery-preventing-bar-code inks, light-absorption inks, light-absorption paints, marking agents for positioning photographs and films, dyeing agents for assorting plastics when in recycling, preheating supplemental agents for shaping and processing PET bottles, effective ingredients for pharmaceuticals to treat tumors in general regarded as being susceptible to the visible light, and ingredients for assisting the function of such effective ingredients.

Although the methine dyes of the present invention have distinct light tolerance against environmental light such as natural and artificial light, the present invention should never exclude the embodiments, where the methine dyes are optionally used in combination with one or more of so called light-tolerance improvers or quenchers to inhibit, for example, the fading, deterioration, denaturing, quality change, decomposition, or the like of the methine dyes induced by singlet oxygen which may be generated by radiation such as of laser beams, when the methine dyes are applied to the above-identified uses. Examples of the light-tolerance improvers usable in combination with the methine dyes of the present invention include amine compounds, carotenoid compounds, sulfide compounds, phenol compounds, and metal complexes including inorganic complex chelate complexes and organic metal complexes such as of acetylacetonatochelate, salicylaldehyde oxime, diimmonium, dithiol, thiocatecholchelate, thiobisphenolatechelate, bisdithio-$\alpha$-diketone chelate, and formazan, all of which can be optionally used in an appropriate combination. Among which metal complexes of formazan and dithiol are most preferable because they distinctly improve the light tolerance of the methine dyes of the present invention and they realize satisfactory amorphous solids when in mixture conditions with the methine dyes. Depending on use, the amount of light-tolerance improver(s) to be used with the methine dye(s) is usually increased or decreased within the range of at least one percent by weight, preferably, 3 to 30% by weight to the weight of the methine dye(s). When used in combination with light-tolerance improvers, the methine dyes of the present invention are either previously mixed to homogeneity with light-tolerance improvers into a liquid, semi-solid or solid composition form and then applied to objective products; or mixed with light-tolerance improvers while increasing or decreasing their composition ratios in the objective products to the desired range and applied to the desired products after processed into a liquid, semi-solid, or solid form.

As described above, the indolenine compounds of the present invention are useful as intermediates to produce the methine dyes of the present invention. Since the indolenine compounds absorb the light in the ultra violet region, usually, the light with a wavelength of 200 to 350 nm, they can be advantageously useful in ultra violet-cut-filters for optical displays such as computer monitors and television screens; electron-donating dyes for thermal recording papers and pressure-sensitive papers; paints such as paints for coating automobiles, external house paints, paints for covered electric wires, and magnetic paints; inks for ball-point pens, fountain pens, dot printers, printer toners, inkjets, permanent markers, drying-elimination markers, newspaper printings, magazine printings, and laser jet printers; windows; apparatuses for eyes such as lens for glasses, telescopes, goggles, hand shields, contact lenses, and intraocular lenses.

The methine dyes of the present invention substantially absorb the light in the ultra violet to the infrared regions, usually, in the region with wavelengths of longer than 300 nm, particularly, in the region with wavelengths of 350 to 850 nm, more particularly, in the region with wavelengths of around 350 to 450 nm, 630 to 680 nm, and 750 to 800 nm, and have relatively high light-tolerance against environmental light of natural and artificial light, and therefore the methine dyes are particularly useful as absorption materials for composing recording layers for high-density optical recording media with a capacity of 15 to 23.3 GB per side such as BD-Rs and HD DVD-Rs using laser beams with wavelengths of 800 nm or lower, particularly, around 350 to 450 nm as a recording light, DVD-Rs using laser beams with wavelengths of 630 to 680 nm as a recording light, and CD-Rs using laser beams with wavelengths of around 750 to 800 nm as a recording light.

Explaining the use of the methine dyes of the present invention in optical recording media, the methine dyes do not require any particular treatment or handling when used in the optical recording media, and the optical recording media according to the present invention can be prepared in accordance with conventional optical recording media: One or more of the methine dyes of the present invention as light-absorbing materials can be optionally mixed with one or more other light-absorbing materials to control the reflectance and the optical absorption efficiency in recording layers; or, to improve processability and performance of the objective optical recording media, admixed with one or more light-resistant improvers, binders, dispersing agents, flame retardants, lubricants, antistatic agents, surfactants, and plasticizers, followed by dissolving the mixtures in organic solvents, homogeneously coating the solutions over either surface of substrates in such a manner of using spraying, soaking, roller coating, or rotatory coating method, drying the applied solutions to form thin layers as recording layers of light-absorbing materials, and optionally either forming reflection layers to be closely attached unto the recording layers, which are made of metals such as gold, silver, copper, platinum, aluminum, cobalt, tin, nickel, iron, and chromium or made of widely-used materials for organic reflection layers, by means of vacuum deposition, chemical vapor deposition, sputtering, or ion-plating method to impart a reflection efficiency of 45% or more, and desirably 55% or more; or, to protect the recording layers from scratches, dusts, stains, etc., rotatory coating the recording layers with ultra violet ray hardening resins or thermosetting resins, which contain flame retardants, stabilizers, and/or antistatic agents, and then hardening the coatings by either irradiating light or heating to form protection layers to be closely attached to the reflection layers.

The light-resistant improvers usable in the present invention are, for example, nitroso compounds such as nitrosodiphenylamine, nitrosoaniline, nitrosophenol, and nitrosonaphthol; tetracyanoquinonedimethane compounds; diimmonium salts; "NKX-1199" (bis[2'-chloro-3-methoxy-4-(2-methoxyethoxy)dithiobenzyl]nickel) produced by Hayashibara Biochemical Laboratories, Inc., Okayama, Japan; and metal complexes such as azo dye metal complexes and formazan metal complexes, all of which can be appropriately used in combination, if necessary. Preferable light-resistant improvers are those which contain nitroso compounds or formazan metal complexes, and most preferable ones are nitroso compounds which have a phenylpyridylamine skeleton as disclosed in Japanese Patent Publication No. 2000-344750, titled "Phenylpyridylamine derivatives" applied for by the same applicant as the present invention, and others composed of metal complexes with metals such as nickel, zinc, cobalt, iron, copper, or palladium, which contain, as ligands, one or more formazan compounds, where pyridine ring is bound to the C-5 of formazan skeleton and pyridine ring or furan ring is bound to the C-3 of formazan skeleton, and their tautomers, disclosed in Published PCT Application No. WO 00/075111, titled "Formazan metal complex". When used in combination with these light-resistant improvers, the methine dyes of the present invention can be effectively prevented from undesired changing of deterioration, fading, color change, and quality change, which are inducible by the exposure to reading- and environmental-lights, without lowering the solubility of the methine dyes in organic solvents and substantially deteriorating preferable optical characteristics. As preferred composition ratios, usually, 0.01 to 5 moles, and preferably 0.1 to 1 mole of a light-resistant improver(s) are incorporated into one mole of the present methine dye(s) while increasing or decreasing the ratio within the range.

Since the methine dyes of the present invention exert a desired solubility in various types of organic solvents without causing any actual problem, there is no restriction of organic solvents used in applying the methine dyes to substrates.

In preparing the optical recording media according to the present invention, any solvents can be selected from the following ones and optionally they can be appropriately used in combination: 2,2,3,3-Tetra fluoro-1-propanol (TFP) commonly used in preparing optical recording media and others, for example, hydrocarbons such as hexane, cyclohexane, methylcyclohexane, dimethylcyclohexane, ethylcyclohexane, isopropylcyclohexane, tert-butylcyclohexane, octane, cyclooctane, benzene, toluene, and xylene; halogen compounds such as carbon tetrachloride, chloroform, 1,2-dichloroethane, 1,2-dibromoethane, trichloroethylene, tetrachloroethylene, chlorobenzene, bromobenzene, and α-dichlorobenzene; alcohols and phenols such as methanol, ethanol, 2,2,2-trifluoroethanol, 1-propanol, 2-propanol, 1-methoxy-2-propanol, 1-ethoxy-2-propanol, 1-butanol, 1-methoxy-2-butanol, 3-methoxy-1-butanol, 4-methoxy-1-butanol, isobutyl alcohol, pentyl alcohol, isopentyl alcohol, cyclohexanol, 2-methoxyethanol (methyl cellosolve), 2-ethoxyethanol (ethyl cellosolve), 2-isopropoxy-1-ethanol, diethylene glycol, triethylene glycol, propylene glycol, glycerine, phenol, benzyl alcohol, cresol, and diacetone alcohol; ethers such as diethyl ether, diisopropyl ether, tetra hydrofuran, tetra hydropyran, 1,4-dioxane, anisole, 1,2-dimethoxyethane, diethylene glycol dimethyl ether, cyclohexyl-18-crown-6, methyl carbinol, and ethylcarbitol; ketones such as furfural, acetone, ethyl methyl ketone, and cyclohexanone; esters such as ethyl acetate, butyl acetate, ethylene carbonate, propylene carbonate, and trimethyl phosphate; amides such as formamide, N-methyl formamide, N, N-dimethylformamide, and hexamethylphosphoric triamide; nitrites such as acetonitrile, propionitrile, and succinonitrile; nitro compounds such as nitromethane and nitrobenzene; amines such as ethylene diamine, pyridine, piperidine, morpholine, and N-methylpyrrolidone; and sulfur-containing compounds such as dimethylsulfoxide and sulfolane.

Particularly, since the methine dyes of the present invention have a relatively-high solubility in easily-volatile organic solvents such as TFP, diacetone alcohol, methyl cellosolve, and ethyl cellosolve, they are substantially free from inducing crystallization and causing inconsistency of thickness and surface of the layers formed on optical recording media, even when dried after dissolved in the above-identified organic solvents and coated on substrates. The methine dyes of the present invention well dissolve in non-halogen solvents, for example, alcohols such as methyl cellosolve, ethyl cellosolve, and diacetone alcohol; and ketones such as cyclohexanone. When used in dissolving and coating the methine dyes on substrates, the above alcohols neither damage the substrates nor substantially pollute the environment because they are non-halogen solvents.

Conventional substrates can be used in the present invention, and usually the substrates used in the present invention can be processed with appropriate materials, for example, processed into discs, 12 cm in diameter and 0.6 mm or 1.2 mm in thickness, to suit to final uses by the methods such as compression molding, injection molding, compression-injection molding, photopolymerization method (2P method), thermosetting integral method, and lightsetting integral method. Such discs can be used in a single or multiple manner after being appropriately attached together with adhesives or adhesive sheets, etc. In principal, any materials for substrates can be used in the present invention as long as they are substantially transparent and have a transmittance of at least 80%, and preferably at least 90% over the wavelength ranging from 300 nm to 800 nm. Respective examples of such materials are glass, ceramics, and others including plastics such as polyacrylate, poly(methyl methacrylate), polycarbonate, polystyrene (styrene copolymer), polymethylpentene, polyester, polyolefin, polyimide, polyetherimide, polysulfone, polyethersulfone, polyarylate, polycarbonate/polystyrene alloy, polyestercarbonate, polyphthalatecarbonate, polycarbonateacrylate, non-crystalline polyolefin, methacrylate copolymer, diallylcarbonatediethylene-glycol, and epoxy resin, among which polycarbonate is usually used. In the case of plastic substrates, concaves for expression of synchronizing signals and addresses of tracks and sectors are usually transferred to the internal circle of the tracks during their formation. The form of concaves are not specifically restricted, and preferably they are formed to give 0.2 to 1.8 μm in average wide and 70 to 200 nm in width.

Considering the viscosity, the light-absorbing materials containing the methine dyes of the present invention are prepared into 0.5 to 5% (w/w) solutions in the organic solvents as mentioned above, and then uniformly coated over substrates to form a recording layer, 10 to 1,000 nm, and preferably 50 to 300 nm in thickness, after dried. Prior to coating the solutions, preliminary layers can be formed over the substrates to improve the protection and adhesion ability of the substrates, if necessary. Materials for the preliminary layers are, for example, high-molecular substances such as ionomer resins, polyamide resins, vinyl resins, natural resins, silicon, and liquid rubbers. In the case of using binders, the following polymers can be used alone or in combination in a weight ratio of 0.01 to 10 times by weight of the methine dye(s):

Cellulose esters such as nitrocellulose, cellulose phosphate, cellulose sulfate, cellulose acetate, cellulose propionate, cellulose lactate, cellulose palmitate, and cellulose acetate/propionate; cellulose ethers such as methyl cellulose, ethyl cellulose, propyl cellulose, and butyl cellulose; vinyl resins such as polystyrene, poly(vinyl chloride), poly(vinyl acetate), poly(vinyl acetal), poly(vinyl butyral), poly(vinyl formal), poly(vinyl alcohol), and poly(vinylpyrrolidone); copolymer resins such as styrene-butadiene copolymers, styrene-acrylonitrile copolymers, styrene-butadiene-acrylonitrile copolymers, vinyl chloride-vinyl acetate copolymers, and maleic anhydride copolymers; acrylic resins such as poly(methylmethacrylate), poly(methyl acrylate), polyacrylate, polymethacrylate, polyacrylamide, and polyacrylonitrile; polyesters such as poly(ethylene terephthalate); and polyolefins such as polyethylene, chlorinated polyethylene, and polypropylene.

Explaining the method for using the optical recording media according to the present invention, for example, the high-density optical recording media such as BD-Rs and HD DVD-Rs with a recording capacity of 15 to 23.3 GB per side and other optical recording media such as DVD-Rs and CD-Rs according to the present invention can write various information at a relatively-high density by using a laser beam with a wavelength of 850 nm or shorter, and particularly 350 to 450 nm, 630 to 680 nm, or 750 to 800 nm irradiated by semiconductor lasers such as those of GaN, AlGaInP, GaAsP, GaAlAs, InGaP, InGaAsP or InGaAlP; or Nd-YAG lasers combined with second harmonic generation inducing elements (SHG elements) such as distributed feed back and Bragg reflection types of elements. Laser beams with wavelengths similar to or slightly longer than those used for writing information are used to read recorded information. As for the laser power for writing and reading information, in the optical recording media of the present invention, it is preferably set to a relatively-high level that exceeds the threshold of the energy required for forming marks when used for writing information, while it is desirably set to a relatively-low level below the threshold, when used for reading the recorded information, although the power levels vary depending on the type and ratio of light-resistant improvers used in combination with the methine dyes. Generally, the levels can be controlled to powers of over 1 mW but not higher than 50 mW for writing, and controlled to powers of 0.1 to 4 mW for reading. The recorded information is read out by detecting the changes of the reflection light level or the transmission light level in both the parts with or without marks to be formed on the recording surfaces of optical recording media.

Accordingly, in the present optical recording media, minute pits with marks, at a track pitch of 1.6 μm or lower and a mark length of 0.9 μm or lower, formed by using a light pickup by a laser beam with a wavelength of around 350 to 450 nm, 630 to 680 nm, or 750 to 800 nm. For example, using a disk substrate, 12 cm in diameter, it can realize an extremely-high density optical recording medium with an optical recording capacity of 0.7 GB per one side when a laser beam with a wavelength of around 750 to 800 nm is used, an optical recording capacity of 4.7 GB per one side when a laser beam with a wavelength of around 630 to 680 nm is used, or with an optical recording capacity of 15 to 23.3 GB per one side when a laser beam with a wavelength of around 350 to 450 nm is used.

Since the optical recording media of the present invention can record information of characters, images, voices, and other digital data at a relatively-high density, they are extremely useful as recording media for professional and family use to record and backup/keep documents, data, and computer softwares. Particular examples of the types of industries and the forms of information to which the optical recording media can be applied are as follows: Drawings of constructions and engineering works, maps, ledgers of loads and rivers, aperture cards, architectural sketches, documents of disaster protection, wiring diagrams, arrangement plans, information of news papers and magazines, local information, and construction reports, which are all used for constructions and engineering works; blueprints, ingredient tables, prescriptions, product specifications, product price tables, part's lists, information for maintenance, case study files of accidents and troubles, manuals for claims, production schemes, technical documents, sketches, details, company's house-made products files, technical reports, and analysis reports, which are all used in productions; users' information, customers information, company information, contracts, information of news papers and magazines, business reports, company information, inquiry into the financial status of enterprises, and stock lists, which are all used for sales; company information, stock records, statistical documents, information of news papers and magazines, contracts, customers' lists, documents of application/notification/licenses/authorization, and business reports, which are all used in money; information of real properties, sketches of constructions, maps, local information, information of news papers and magazines, contracts for leases, information of companies, stock lists, traffic information, information of customers, which are all used for real property and transportations; diagrams of writings and pipes, documents of disaster protection, tables of operation manuals, documents of investigations, and technical reports, which are all used for electric and gas supplies; medical cartes, files of clinical histories and case studies, and diagrams for medical care/institution relationships, which are all used for medical fields; scientific papers, records in academic societies, monthly reports of researches, data of researches, documentary records and indexes thereof, which are all used in universities, colleges, and research institutes; inspection data, literatures, patent publications, weather maps, analytical records of data, and customer's files, which are all used for information; case studies on laws; membership lists, history notes, records of works/products, competition data, and data of meetings/congresses, which are all used for organizations/associations; sightseeing information and traffic information, which are all used for sightseeing; indexes of homemade publications, information of news papers and magazines, who's who files, sport records, telop files, and scripts, which are all used in mass communications and publishers; and maps, ledgers of roads and livers, fingerprint files, resident cards, documents of application/notification/license/authorization, statistical documents, and public documents, which are all used in government offices. Particularly, the write-once type optical recording media of the present invention can be advantageously useful for storing records of cartes and official documents, and used as electric libraries for art galleries, libraries, museums, broadcasting stations, etc.

As a rather specific use, the optical recording media of the present invention can be used to edit or proof compact discs, digital video discs, laser discs, MD (a mini disc as an information recording system using a photomagnetic disc), CDV (a laser disc using a compact disc), DTA (an information recording system using a magnetic tape), CD-ROM (a read-only memory using a compact disc), DVD-ROM (a read-only memory using a digital video disc), DVD-RAM (a writable and readable memory using a digital multi-use disc), digital photos, movies, video softwares, audio softwares, computer graphics, publishing products, broadcasting programs, commercial messages, game softwares, etc.; and used as external program recording means for large-sized computers and car navigation systems.

The term "optical recording media" as referred to as in the present invention mean optical recording media in general which use the properties of the methine dyes of the present invention that substantially absorb light with a wavelength of 850 nm or shorter, particularly, around 350 to 450 nm, 630 to 680 nm or 750 to 800 nm; and include, in addition to organic ablation type optical recording media, those which use thermal coloration method using the chemical reaction between coloring agents and developers induced by heat that is generated when the methine dyes absorb light; or using the technique called "moth-eye type technique" which uses the phenomenon where the above heat smooths the pattern of periodical unevenness provided on the surface of the substrates.

The following examples describe the preferred embodiments according to the present invention:

Example 1

Indolenine Compound

Forty grams of the compound represented by Chemical Formula 54 and 76.6 g of the compound represented by Chemical Formula 55 were placed in a reaction container and allowed to react for one hour while stirring. The reaction mixture was cooled, admixed with 80 ml of concentrated hydrochloric acid, and allowed to react for 30 min while heating. The resulting reaction mixture was cooled, admixed with a 25% aqueous sodium hydroxide solution drop by drop, and further admixed with chloroform for extraction. The chloroform layer was collected by decantation, washed with water and saturated saline, dehydrated with anhydrous magnesium sulfate, filtered, and followed by removing chloroform. The oily extract thus obtained was purified on silicagel column chromatography using a mixture solution of chloroform and methanol as a developing solvent to obtain 29.8 g of a white, oily product of the indolenine compound represented by Chemical Formula 46 of the present invention.

Chemical Formula 54:

[Chem. 70]

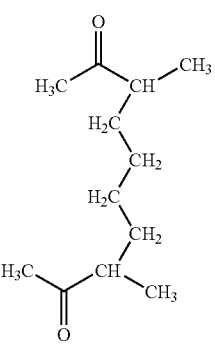

Chemical Formula 55:

[Chem. 71]

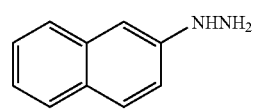

A part of the oily product was sampled and measured for absorption spectrum in methanol solution as an absorption property in usual manner, revealing that the indolenine compound has absorption peaks ($\epsilon$=7.94×10$^3$ to 5.45×10$^4$) in the ultra violet region with wavelengths of around 215 to 305 nm. $^1$H-Nuclear magnetic resonance ($^1$H-NMR) analysis of the indolenine compound in chloroform-d solution gave a chemical shift δ (ppm, TMS) at peaks of 0.15 to 0.21 (2H, m, —CH$_2$—), 0.30 to 0.36 (2H, m, —CH$_2$—), 1.37 (6H, s, CH$_3$—), 1.60 to 1.70 (2H, m, —CH$_2$—), 2.00 to 2.10 (2H, m, —CH$_2$—), 2.14 (6H, s, CH$_3$—), 7.41 to 7.51 (4H, m, ArH), 7.68 to 7.72 (2H, m, ArH), 7.78 to 7.85 (4H, m, ArH), and 7.92 to 7.95 (2H, m, ArH).

The indolenine compound is useful as an intermediate to prepare the methine dyes with a bis-indolenine skeleton. Since the indolenine compound absorbs the light in the ultra violet region, it is also useful as an ultra violet absorbing agent in ultra violet-cut-filters, dyes, inks, and ophthalmic devices.

Example 2

Indolenine Compound

Except for using the compound represented by Chemical Formula 56 in place of the compound represented by Chemical Formula 54, it was allowed to react similarly as in Example 1 to obtain 8.3 g of a white, oily product of the indolenine compound represented by Chemical Formula 51 of the present invention.

Chemical Formula 56:

[Chem. 72]

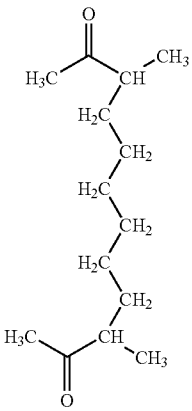

A part of the oily product was sampled and measured for absorption spectrum in methanol solution as an absorption property in usual manner, revealing that the indolenine compound has absorption peaks ($\epsilon$=8.35×10$^3$ to 5.81×10$^4$) in the ultra violet region with wavelengths of around 215 to 305 nm. $^1$H-NMR Analysis of the indolenine compound in chloroform-d solution gave a chemical shift δ (ppm, TMS) at peaks of 0.10 to 0.25 (2H, m, —CH$_2$—), 0.30 to 0.45 (2H, m, —CH$_2$—), 0.70 to 0.85 (4H, m, —CH$_2$—), 1.43 (6H, s, CH$_3$—), 1.74 to 1.84 (2H, m, —CH$_2$—), 2.12 to 2.22 (2H, m, —CH$_2$—), 2.20 (6H, s, CH$_3$—), 7.38 to 7.51 (4H, m, ArH), and 7.70 to 7.92 (8H, m, ArH).

The indolenine compound is useful as an intermediate to prepare the methine dyes with a bis-indolenine skeleton. Since the indolenine compound absorbs the light in the ultra violet region, it is also useful as an ultra violet absorbing agent in ultra violet-cut-filters, dyes, inks, and ophthalmic devices.

Example 3

Indolenine Compound

Except for using the compound represented by Chemical Formula 57 in place of the compound represented by Chemical Formula 54, it was allowed to react similarly as in Example 1 to obtain 12.8 g of a white, oily product of the indolenine compound represented by Chemical Formula 47 of the present invention.

Chemical Formula 57:

[Chem. 73]

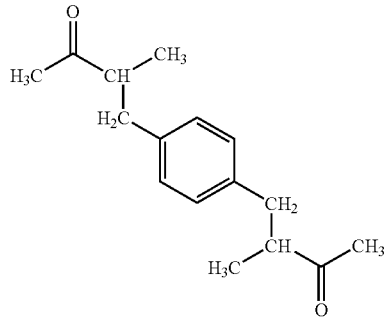

A part of the oily product was sampled and measured for absorption spectrum in methanol solution as an absorption property in usual manner, revealing that the indolenine compound has absorption peaks in the ultra violet region with wavelengths of around 216 to 350 nm. $^1$H-NMR Analysis of the indolenine compound in chloroform-d solution gave a chemical shift δ (ppm, TMS) at peaks of 1.52 (6H, s, $CH_3$), 2.20 (6H, s, $CH_3$), 3.00 (2H, d, $CH_2$—), 3.38 (2H, d, $CH_2$), 6.01 (4H, s, ArH), 7.25 to 7.56 (6H, m, ArH), 7.74 (2H, d, ArH), 7.91 (2H, d, ArH), and 7.98 (2H, d, ArH).

The indolenine compound is useful as an intermediate to prepare the methine dyes with a bis-indolenine skeleton. Since the indolenine compound absorbs the light in the ultra violet region, it is also useful as an ultra violet absorbing agent in ultra violet-cut-filters, dyes, inks, and ophthalmic devices.

Although the indolenine compounds of the present invention slightly vary in their production conditions and yields depending on their structures, any of the indolenine compounds including the Chemical Formulae 46 to 53 other than the above identified compounds can be obtained in a desired yield by the methods in Examples 1 to 3 or in accordance therewith.

Example 4

Methine Dye

In a reaction container were placed 12.5 g of the compound represented by Chemical Formula 46 and 16.9 g of ethyl p-toluenesulfonate, and the mixture was heated for 3.5 hours while stirring, admixed with 125 ml of acetone drop by drop, and cooled to obtain 16.65 g of a white crystal of the compound represented by Chemical Formula 58.

Chemical Formula 58:

[Chem. 74]

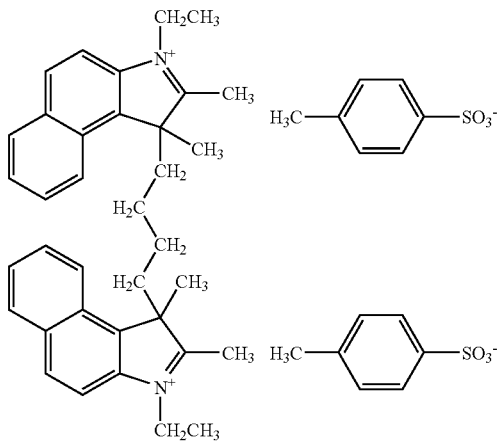

An adequate amount of acetonitrile was placed in a reaction container, admixed with 1.5 g of the previously obtained compound represented by Chemical Formula 58, 1.82 g of the compound represented by Chemical Formula 59, and 0.75 ml of acetic anhydride, and allowed to react for 30 min under heating and stirring conditions, followed by adding 0.99 ml of triethylamine to the reaction mixture and heating and stirring it for 1.5 hours. To the mixture was added an adequate amount of isopropyl ether, followed by removing the supernatant by decantation and refluxing the resultant for 30 min under heating conditions after addition of 15 ml of methanol. Thereafter, the reaction mixture was admixed with eight milliliters of a methanol solution with 0.87 g of ammonium hexa fluorophosphate drop by drop and cooled to obtain 1.37 g of a brown crystal of the methine dye represented by Chemical Formula 1 of the present invention.

Chemical Formula 59:

[Chem. 75]

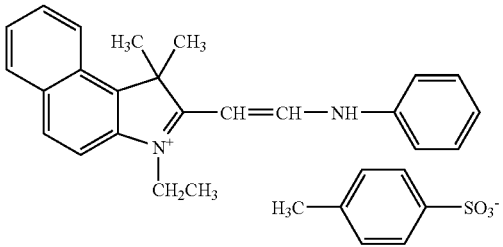

A part of the crystal was sampled and measured on DSC analysis for melting point and decomposition point as thermal properties, revealing that the methine dye has a melting point of about 252° C. and a decomposition point of about 300° C. Conventional measurement of the dye for visible absorption spectrum in methanol solution as an absorption property gave a main absorption maximum at a wavelength of about 544 nm (E=1.94×10$^5$). $^1$H-NMR Analysis of the methine dye in dimethyl sulfoxide-d$^6$ solution gave a chemical shift δ (ppm, TMS) at peaks of 0.15 to 0.32 (2H, m, —$CH_2$—), 0.65 to 0.82 (2H, m, —$CH_2$—), (6H, t, $CH_3$—), 1.23 (6H, t, $CH_3$—), 1.62 (6H, s, $CH_3$—), 1.80 (6H, s, $CH_3$—), 1.87 (6H, s, $CH_3$—), 1.85 to 2.07 (2H, m, —$CH_2$—), 2.70 to 2.90 (2H, m, —$CH_2$—), 3.95 to 4.20 (8H, m, —$CH_2$—), 6.39 (2H, d, —CH=), 6.48 (2H, d, —CH=), 7.51 (2H, t, ArH), 7.59 (2H, t, ArH), 7.61 (2H, d, ArH), 7.66 (2H, t, ArH), 7.75 (2H, d, ArH), 7.78 (2H, t, ArH), 8.01 (4H, t, ArH), 8.13 (4H, t, ArH), 8.16 (2H, d, ArH), 8.24 (2H, d, ArH), and 8.32 (2H, t, —CH=).

Since the methine dye of the present invention efficiently absorbs the light with wavelengths of around 500 to 600 nm in the visible region and has improved solubility in solvents and satisfactory thermal property, it is useful as light-absorption material for absorbing the light in the visible region to shield it or to use the energy of the light in the visible region when used in the fields of information recordings, solar energy generations, electric machineries and devices, electric communication apparatuses, optical apparatuses, clothes, building/bedding/decorating products, sanitary and health goods, and agricultural materials.

Example 5

Methine Dye

Except for using the compound represented by Chemical Formula 60 in place of the compound represented by Chemical Formula 59, it was reacted similarly as in Example 4 to obtain 1.71 g of a brown crystal of the methine dye represented by Chemical Formula 2 of the present invention.

Chemical Formula 60:

[Chem.76]

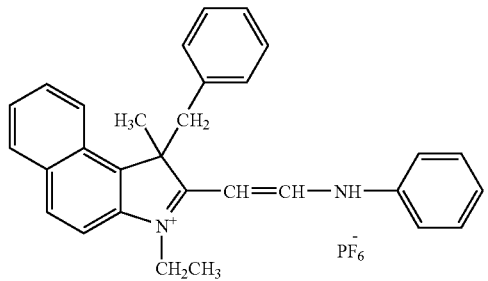

A part of the crystal was sampled and measured on DSC analysis for melting point and decomposition point as thermal properties, revealing that the methine dye gave a decomposition point of about 211° C. undistinguishable from its melting point. Conventional measurement of the methine dye for visible absorption spectrum in methanol solution as an absorption property gave a main absorption maximum at a wavelength of about 551 nm ($\epsilon=1.87\times10^5$). $^1$H-NMR Analysis of the methine dye in dimethyl sulfoxide-$d_6$ solution gave a chemical shift δ (ppm, TMS) at peaks of 0.10 to 0.30 (2H, m, —CH$_2$—), 0.70 to 0.90 (2H, m, —CH$_2$—), 0.50 to 1.30 (12H, m, CH$_3$—), 1.50 to 2.00 (16H, m, CH$_3$—, —CH$_2$—), 1.90 to 2.10 (2H, m, —CH$_2$—), 2.80 to 3.00 (2H, m, —CH$_2$—), 3.80 to 4.20 (8H, m, —CH$_2$—), and 5.90 to 8.50 (40H, m, ArH, —CH=).

Since the methine dye of the present invention efficiently absorbs the light with wavelengths of around 500 to 600 nm in the visible region and has improved solubility in solvents and satisfactory thermal property, it is useful as a light-absorption material for absorbing the light in the visible region to shield it or to use the energy of the light in the visible region when used in the fields of information recordings, solar energy generations, electric machineries and devices, electric communication apparatuses, optical apparatuses, clothes, building/bedding/decorating products, sanitary and health goods, and agricultural materials.

Example 6

Methine dye

Except for using the compound represented by Chemical Formula 61 in place of the compound represented by Chemical Formula 59, it was reacted similarly as in Example 4 to obtain 1.37 g of a green crystal of the methine dye represented by Chemical Formula 3 of the present invention.

Chemical Formula 61:

[Chem. 77]

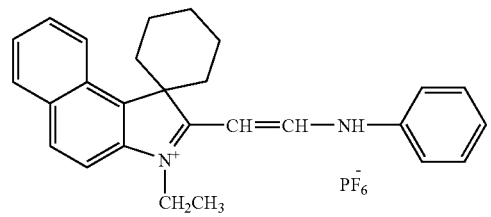

A part of the crystal was sampled and measured on DSC analysis for melting point and decomposition point as thermal properties, revealing that the methine dye has a decomposition point of about 235° C. undistinguishable from its melting point. Conventional measurement of the methine dye for visible absorption spectrum in methanol solution as an absorption property gave a main absorption maximum at a wavelength of about 551 nm ($\epsilon=1.92\times10^5$). $^1$H-NMR Analysis of the methine dye in dimethyl sulfoxide-$d_6$ solution gave a chemical shift δ (ppm, TMS) at peaks of 0.00 to 0.20 (2H, m, —CH$_2$—), 0.60 to 0.75 (2H, m, —CH$_2$—), 1.21 (6H, t, CH$_3$—), 1.33 (6H, t, CH$_3$—), 1.45 to 2.10 (18H, m, —CH$_2$—), 1.78 (6H, s, CH$_3$—), 2.25 to 2.50 (4H, m, —CH$_2$—), 2.60 to 2.80 (2H, m, —CH$_2$—), 4.00 to 4.12 (4H, m, —CH$_2$—), 4.12 to 4.22 (4H, m, —CH$_2$—), 6.56 (2H, d, —CH=), 6.72 (2H, d, —CH=), 7.48 to 7.72 (12H, m, ArH), and 7.98 to 8.21 (14H, m, ArH, —CH=).

Since the methine dye of the present invention efficiently absorbs the light with wavelengths of around 500 to 600 nm in the visible region and has improved solubility in solvents and satisfactory thermal property, it is useful as a light-absorption material for absorbing the light in the visible region to shield it or to use the energy of the light in the visible region when used in the fields of information recordings, solar energy generations, electric machineries and devices, electric communication apparatuses, optical apparatuses, clothes, building/bedding/decorating products, sanitary and health goods, and agricultural materials.

Example 7

Methine Dye

Except for using the compounds represented by Chemical Formulae 47 and 60 in place of the respective compounds represented by Chemical Formulae 46 and 59, it was reacted similarly as in Example 4 to obtain 10.47 g of a dark blue crystal of the methine dye represented by Chemical Formula 36 of the present invention.

A part of the crystal was sampled and measured on DSC analysis for melting point and decomposition point as thermal properties, revealing that the methine dye has a decomposition point of about 220° C. undistinguishable from its melting point. Conventional measurement of the methine dye for visible absorption spectrum in methanol solution as an absorption property gave a main absorption maximum at a wavelength of around 599 nm ($\epsilon=1.54\times10^5$). $^1$H-NMR Analysis of the methine dye in dimethyl sulfoxide-$d_6$ solution gave a chemical shift δ (ppm, TMS) at peaks of 0.7 to 0.9 (6H, m), 2.0 to 2.2 (12H, m), 3.2 to 3.6 (10H, m), 3.9 to 4.2 (8H, m), and 6.0 to 8.8 (44H, m).

Since the methine dye of the present invention efficiently absorbs the light with wavelengths of around 500 to 600 nm in the visible region and has improved solubility in solvents and satisfactory thermal property, it is useful as a light-absorption material for absorbing the light in the visible region to shield it or to use the energy of the light in the visible region when used in the fields of information recordings, solar energy generations, electric machineries and devices, electric communication apparatuses, optical apparatuses, clothes, building/bedding/decorating products, sanitary and health goods, and agricultural materials.

Example 8

Methine Dye

In a reaction container were respectively placed 2.0 g of the compound represented by Chemical Formula 51 and 2.54 g of ethyl p-toluenesulfonate, and the mixture was heated for two hours while stirring, admixed with 20 ml of acetone drop by drop, and cooled to obtain 2.64 g of a white crystal of the compound represented by Chemical Formula 62.

Chemical Formula 62:

[Chem. 78]

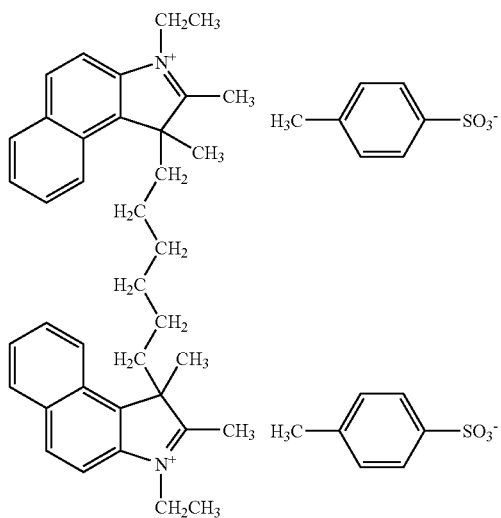

An adequate amount of acetonitrile was placed in a reaction container, admixed with 2.0 g of the previously obtained compound represented by Chemical Formula 62, 2.35 g of the compound represented by Chemical Formula 59, and 0.97 ml of acetic anhydride, and allowed to react for 30 min under heating and stirring conditions, followed by adding 1.28 ml of triethylamine to the reaction mixture and heating and stirring it for 1.0 hour. To the mixture was added an adequate amount of isopropyl ether, followed by removing the supernatant by decantation and refluxing the resultant for 30 min under heating conditions after addition of 20 ml of methanol. Thereafter, the reaction mixture was admixed with five milliliters of a methanol solution with 1.12 g of ammonium hexa fluorophosphate drop by drop and cooled to obtain 2.31 g of a dark blue crystal of the methine dye represented by Chemical Formula 8 of the present invention.

A part of the crystal was sampled and measured on DSC analysis for melting point and decomposition point as thermal properties, revealing that the methine dye has a melting point of about 251° C. and a decomposition point of about 30° C. Conventional measurement of the dye for visible absorption spectrum in methylene chloride solution as an absorption property gave a main absorption maximum at a wavelength of about 545 nm ($\epsilon=1.79\times10^5$). $^1$H-NMR Analysis of the methine dye in dimethyl sulfoxide-$d_6$ solution gave a chemical shift δ (ppm, TMS) at peaks of 0.00 to 0.20 (2H, m, —$CH_2$—), 0.50 to 0.65 (2H, m, —$CH_2$—), 0.65 to 0.80 (4H, m, —$CH_2$—), 1.25 (6H, t, $CH_3$—), 1.35 (6H, t, $CH_3$—), 1.72 (6H, s, $CH_3$—), 1.87 (6H, s, $CH_3$—), 1.91 (6H, s, $CH_3$—), 2.00 to 2.20 (2H, m, —$CH_2$—), 2.60 to 2.75 (2H, m, —$CH_2$—), 4.15 to 4.30 (8H, m, —$CH_2$—), 6.49 (2H, d, —CH=), 6.51 (2H, d, —CH=), 7.38 (2H, t, ArH), 7.54 (4H, m, ArH), 7.67 (4H, m, ArH), 7.78 (2H, t, ArH), 7.89 (2H, d, ArH), 7.96 (2H, d, ArH), 8.06 to 8.16 (6H, m, ArH), 8.20 (2H, d, ArH), and 8.24 (2H, t, —CH=).

Since the methine dye of the present invention efficiently absorbs the light with wavelengths of around 500 to 600 nm in the visible region and has improved solubility in solvents and satisfactory thermal property, it is useful as a light-absorption material for absorbing the light in the visible region to shield it or to use the energy of the light in the visible region when used in the fields of information recordings, solar energy generations, electric machineries and devices, electric communication apparatuses, optical apparatuses, clothes, building/bedding/decorating products, sanitary and health goods, and agricultural materials.

Example 9

Methine Dye

An adequate amount of acetonitrile was placed in a reaction container, admixed with 5.0 g of the compound represented by Chemical Formula 63, 7.44 g of the compound represented by Chemical Formula 64, and 7.37 ml of triethylamine, followed heating and stirring the mixture for 30 min. After the addition of an adequate amount of isopropyl alcohol, the resulting mixture was cooled and filtered to collect the precipitated crystal. To a reaction container were added the crystal thus obtained and an adequate amount of methanol, and the mixture was refluxed for 30 min under heating and stirring conditions. Thereafter, the reaction mixture was admixed with an aqueous solution with 4.5 g of sodium perchlorate drop by drop and cooled to obtain 3.17 g of a brown color crystal of the methine dye represented by Chemical Formula 21 of the present invention.

Chemical Formula 63:

-continued

[Chem. 79]

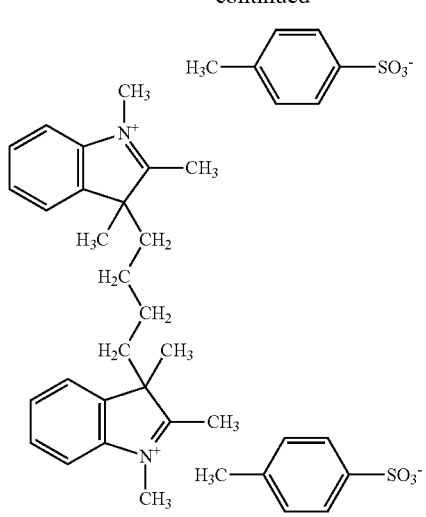

Chemical Formula 63:

[Chem. 80]

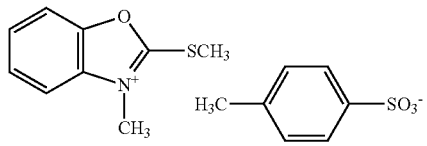

A part of the crystal was sampled and measured on DSC analysis for melting point and decomposition point as thermal properties, revealing that the methine dye has a decomposition point of about 285° C. undistinguishable from its melting point. Conventional measurement of the methine dye for visible absorption spectrum in methanol solution as an absorption property gave a main absorption maximum at a wavelength of about 415 nm ($\epsilon$=5.52×10$^5$). $^1$H-NMR Analysis of the methine dye in dimethyl sulfoxide-d$_6$ solution gave a chemical shift δ (ppm, TMS) at peaks of 0.20 to 0.30 (2H, m, —CH$_2$—), 0.40 to 0.50 (2H, m, —CH$_2$—), 1.64 (6H, s, CH$_3$—), 1.80 to 2.00 (2H, m, —CH$_2$—), 2.70 to 2.90 (2H, m, —CH$_2$—), 3.50 (6H, s, CH$_3$—), 3.65 (6H, s, CH$_3$—), 5.55 (2H, s, —CH=), and 7.20 to 7.80 (20H, m, ArH).

Since the methine dye of the present invention efficiently absorbs the light with wavelengths of around 400 to 500 nm in the visible region and has improved solubility in solvents and satisfactory thermal property, it is useful as a light-absorption material for absorbing the light in the visible region to shield it or to use the energy of the light in the visible region when used in the fields of information recordings, solar energy generations, electric machineries and devices, electric communication apparatuses, optical apparatuses, clothes, building/bedding/decorating products, sanitary and health goods, and agricultural materials.

Example 10

Methine Dye

To a reaction container were added 5.0 g of the compound represented by Chemical Formula 63 and 2.08 g of N,N'-diphenylformamidine, and the mixture was heated and stirred for three hours. After adding an adequate amount of acetone, the resulting reaction mixture was cooled, followed by collecting the precipitated crystal. To a reaction container were added the obtained crystal and an adequate amount of methanol, the contents were refluxed for 30 min while heating, admixed with an aqueous solution with 4.5 g of sodium perchlorate drop by drop and cooled to obtain 4.19 g of a brown crystal of the methine dye represented by Chemical Formula 24 of the present invention.

A part of the crystal was sampled and measured on DSC analysis for melting point and decomposition point as thermal properties, revealing that the methine dye has a decomposition point of about 300° C. undistinguishable from its melting point. Conventional measurement of the methine dye for visible absorption spectrum in methanol solution as an absorption property gave a main absorption maximum at a wavelength of about 428 nm ($\epsilon$=1.62×10$^5$). $^1$H-NMR Analysis of the methine dye in dimethyl sulfoxide-d$_6$ solution gave a chemical shift δ (ppm, TMS) at peaks of 0.15 to 0.30 (2H, m, —CH$_2$—), 0.65 to 0.82 (2H, m, —CH$_2$—), 1.62 (6H, s, CH$_3$—), 1.82 to 2.02 (2H, m, —CH$_2$—), 2.75 to 2.95 (2H, m, —CH$_2$—), 3.40 (6H, s, CH$_3$—), 6.43 (2H, d, —CH=), 7.20 to 8.20 (22H, m, ArH), and 8.51 (2H, d, —CH=).

Since the methine dye of the present invention efficiently absorb the light with wavelengths of around 400 to 500 nm in the visible region and has improved solubility in solvents and satisfactory thermal property, it is useful as a light-absorption material for absorbing the light in the visible region to shield it or to use the energy of the light in the visible region when used in the fields of information recordings, solar energy generations, electric machineries and devices, electric communication apparatuses, optical apparatuses, clothes, building/bedding/decorating products, sanitary and health goods, and agricultural materials.

Although the methine dyes of the present invention may slightly vary in their production conditions and yields depending on their structures, any of the methine dyes including Chemical Formulae to 45 other than the above-identified compounds can be obtained in a desired yield by the methods in Examples 4 to 10 or in accordance therewith.

Example 11

Solubility of Methine Dye

For the methine dyes of the present invention as listed in Table 1, they were respectively dissolved in 100 ml of TFP at 20° C. and, as solubility, measured for the mass of each methine dye. In parallel, conventionally known related compounds represented by Chemical Formulae 65 to 67 were similarly measured for their solubilities. The results are in Table 1.

TABLE 1

| Methine dye | Solubility (% by weight) | Remarks |
|---|---|---|
| Chemical Formula 1 | 2.06 | The present invention |
| Chemical Formula 2 | 2.68 | The present invention |
| Chemical Formula 3 | 2.47 | The present invention |
| Chemical Formula 8 | 2.58 | The present invention |
| Chemical Formula 36 | 1.66 | The present invention |
| Chemical Formula 65 | 1.10 | Control |
| Chemical Formula 66 | 0.82 | Control |
| Chemical Formula 67 | 0.44 | Control |

Chemical Formula 65:

[Chem. 81]

TABLE 1-continued

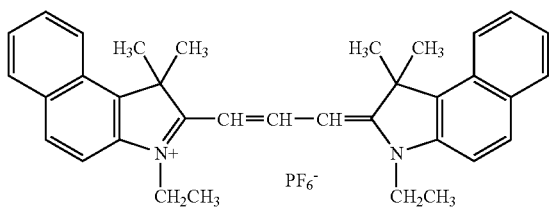

Chemical Formula 66:

[Chem. 82]

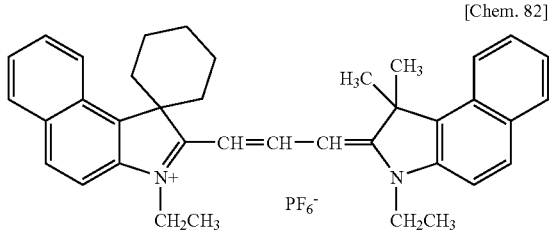

[Chem. 83]

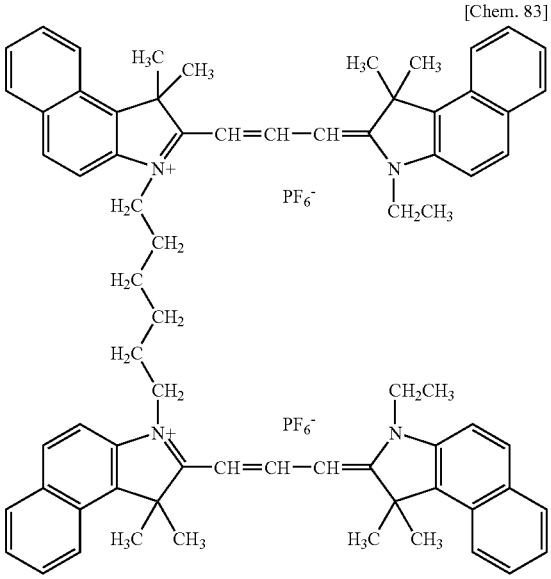

As evident from the result in Table 1, the methine dyes of the present invention showed solubilities in TFP far exceeding those of conventionally known related compounds represented by Chemical Formulae 65 to 67. The solubilities of the conventionally known related compounds were 1.10% or lower, while all of the tested methine dyes of the present invention showed solubilities, exceeding significantly those of the related compounds.

Example 12

Light Tolerance of Cyanine Dye

Any one of the methine dyes represented by Chemical Formulae 1 to 3, 8 and 36, obtained by the methods in Examples 4 to 8, was weighed by 15 mg, added to three milliliters of TFP, and dissolved by energizing with ultra sound for five minutes at ambient temperature. The resulting solution was dropped to homogeneity over either side of a polished glass substrate (5 cm×5 cm) by spin coating, and the substrate was rotated at 1,000 rpm for one minute to homogeneously apply the solution over the substrate, and dried by successively blowing hot air and cool air thereunto in this order to form a thin membrane of any one of the methine dyes of the present invention over the glass substrate.

The transmittance ($T_0$) of the methine dyes in the form of a thin layer was measured at their absorption maximum wavelengths (about 550 nm), and a 7.5 kw xenon lamp was installed apart from the glass substrate at a prescribed distance to expose the glass substrate for two hours with an irradiation energy of 180 W/m$^2$ when measured on the surface of the substrate while blowing cool air thereunto. Thereafter, the transmittance (T) at each of their absorption maximum wavelengths was instantly remeasured, and the residual percentage (%) of each dye was calculated by substituting the measured transmittances T and $T_0$ Formula 1. In parallel, the thin membranes formed with the related compounds represented by Chemical Formulae 65 to 68 were similarly treated as in the above and respectively measured for their transmittances at their absorption maximum wavelengths. The results are in Table 2.

TABLE 2

| Methine dye | Residual percentage (%) of dye | Remarks |
| --- | --- | --- |
| Chemical Formula 1 | 74 | The present invention |
| Chemical Formula 2 | 66 | The present invention |
| Chemical Formula 3 | 64 | The present invention |
| Chemical Formula 8 | 75 | The present invention |
| Chemical Formula 36 | 64 | The present invention |
| Chemical Formula 65 | 73 | Control |
| Chemical Formula 66 | 58 | Control |
| Chemical Formula 67 | 60 | Control |
| Chemical Formula 68 | 50 | Control |

Chemical Formula 68:

[Chem. 84]

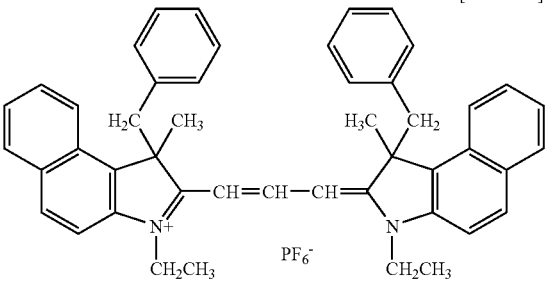

[Formula 1]

$$\text{Residual percentage (\%) of dye} = \frac{100 - T}{100 - T_0} \times 100$$

As found in Table 2, in the thin membrane, as control, consisted of any one of the compounds represented by Chemical Formulae 66 to 68, the compounds changed in a distinct amount with only two hours of exposure and their initial absorbances lowered to 50 to 60% thereof. While, as found in 64 to 75% of the residual percentages of dyes, the thin membrane, constructed by any one of the methine dyes represented by Chemical Formulae 1 to 3, 8 and 36, was relieved of the reduction of light-absorbability, even when exposed similarly as in the control. The thin membrane, as a control membrane, constructed by conventionally known methine dye represented by Chemical Formula 65 gave a roughly similar residual percentage of dye (73%) to those of the methine dyes of the present invention.

These experimental data prove that, compared to conventionally known methine dyes, the methine dyes of the present invention have substantially the same or significantly superior light tolerance in the visible region to those of conventionally known methine dyes.

Example 13

Electric Property of Methine Dye

According to conventional manner, an optical recording medium was prepared by successively multi-layering substrate 1, recording layer 2, reflection layer 3, and protection layer 4 in this order, as shown in FIG. 3. Any one of the methine dyes represented by Chemical Formulae 1 to 3, 8 and 36 in an adequate amount of TFP to give a concentration of 1.6% by weight, and the mixture was heated for awhile, and energized with ultrasonic for dissolution. According to conventional manner, the resulting solution was homogeneously coated over either side of polycarbonate disk substrate 1 (12 cm in diameter, 0.6 mm in thickness) in a rotatory manner and dried to form recording layer 2, made of absorption material, 100 nm in thickness. Thereafter, silver was evaporated unto substrate 1 up to give a layer with 30 to 100 nm in thickness and to form reflection layer 3 to be closely attached to recording layer 2, which was then closely adhered to polycarbonate disk protection layer 4 (12 cm in diameter, 0.6 mm in thickness) to form an optical recording medium for testing. In parallel, except for using the conventionally known methine dye represented by Chemical Formula 65 or 68 in place of the methine dye of the present invention, an optical recording medium as a control was prepared similarly as in the above. No optical recording medium could not be formed with the conventionally known methine dyes, represented by Chemical Formula 66 and 67 because they had a relatively low solubility in TFP and could not be formed into a thin layer.

Using "DDU-1000 MODEL", a commercialized optical disk evaluation apparatus, produced by Pulstech Industries Co., Ltd., Shizuoka, Japan, the seven types of optical recording media were measured for recording sensitivity and electric property (reproduction light power of 0.7 mW) when recorded with test signals of modified 8-16 at a recording light wavelength of 658 nm (NA 0.60) and in data transmission rates of 11.08 Mbps (1× write drive), 44.32 Mbps (4× write drive), and 88.64 Mbps (8× write drive). The results are in Table 3 in parallel.

TABLE 3

| Methine dye | 1 × write drive | | | | 4 × write drive | | | | 8 × write drive | | | | Remarks |
|---|---|---|---|---|---|---|---|---|---|---|---|---|---|
| | PO | Ref. | 14TM | Jitter | PO | Ref. | 14TM | Jitter | PO | Ref. | 14TM | Jitter | |
| Chemical Formula 1 | 8.0 | 70 | 0.67 | 7.5 | 15.0 | 70 | 0.68 | 7.5 | 24.5 | 71 | 0.68 | 7.6 | Present invention |
| Chemical Formula 2 | 8.5 | 65 | 0.69 | 7.4 | 14.5 | 66 | 0.70 | 7.5 | 23.5 | 66 | 0.71 | 7.2 | Present invention |
| Chemical Formula 3 | 8.0 | 58 | 0.60 | 7.8 | 14.0 | 57 | 0.62 | 7.1 | 22.0 | 58 | 0.66 | 6.8 | Present invention |
| Chemical Formula 8 | 8.5 | 70 | 0.68 | 7.6 | 14.5 | 69 | 0.70 | 7.5 | 25.0 | 70 | 0.68 | 7.5 | Present invention |
| Chemical Formula 36 | 7.0 | 53 | 0.58 | 7.4 | 11.0 | 55 | 0.60 | 7.0 | 20.0 | 57 | 0.63 | 6.7 | Present invention |
| Chemical Formula 65 | 12.5 | 72 | 0.68 | 8.0 | 24.5 | 71 | 0.68 | 8.3 | 36.0 | 71 | 0.69 | 8.5 | Control |
| Chemical Formula 66* | — | — | — | — | — | — | — | — | — | — | — | — | Control |
| Chemical Formula 67* | — | — | — | — | — | — | — | — | — | — | — | — | Control |
| Chemical Formula 68 | 10.5 | 60 | 0.64 | 7.8 | 16.5 | 61 | 0.66 | 7.6 | 27.0 | 60 | 0.70 | 7.5 | Control |

Note)
PO: Recording power (mW)
Ref.: Reflection percentage (%)
14TM: 14TM Signal modulation rate
Jitter: Jitter value (ns)
*Not determined because of the low solubilities in TFP of the compounds represented by Chemical Formulae 66 and 67.

The results in Table 3 indicate that, compared with conventionally known methine dyes, the optical recording media prepared with the methine dyes of the present invention attain significantly improved recording powers of optical recording media while retaining the desired electric properties of reflection percentage, modulation rate, and jitter value, independently of recording speeds of 1×, 4× and 8× writing drives. The finding that the methine dyes with a bis-indolenine skeleton according to the present invention improve recording sensitivity was revealed firstly by the present invention. Using the methine dyes of the present invention, it will realize optical recording media with electric properties such as improved sensitivity and jitter.

Example 14

Optical Recording Medium

Any one of the methine dyes represented by Chemical Formulae 1 to 3, 8 and 36 as light-absorption materials was added to TFP to give a concentration of 1.2% by weight per unit volume, and further admixed with a commonly used formazan metal complex as a light-tolerance improver in an amount of 5.0% by weight against the light-absorption material, followed by heating the mixture for a while and energizing it with ultrasonic for dissolution. According to conventional manner, the solution was membrane filtered, homogeneously applied in a rotatory manner over either side of a polycarbonate disk substrate (12 cm in diameter, 1.2 mm in thickness), to which concaves (track pitch of 0.74 μm, 0.03 μm in width, 76 nm in depth) for expressing synchronizing signals and addresses of tracks and sectors had been transferred by injection molding, and dried to form a recording layer, 200 nm in thickness. Thereafter, pure silver was evaporated over the substrate to give a layer with a thickness of 100 nm by spattering method and to form a reflection layer closely attached to the recording layer. The reflection layer was homogeneously applied with "DAICURE CLEAR SD1700", a product name of ultra violet hardening resin commercialized by DIC Corporation, Tokyo, Japan, in a rotatory manner, and irradiated with ultra violet to form a protection layer closely attached to the reflection layer. Thus, five types of optical recording media were prepared. When tested similarly as in Example 13, all the optical recording media according to the present invention exerted substantially the same levels of electric properties such as recording sensitivity, modulation property, reflection percentage, and jitter as those in Example 13.

The optical recording media, having improved electric properties such as recording sensitivity, modulation property, reflection percentage, and jitter, have a recording capacity of over 4 GB and record large amounts of information such as document information, image information, voice information, and other digital information by using a light pickup by a visible light with a wavelength shorter than 700 nm, particularly, a laser beam with a wavelength of around 630 to 680 nm. An electron microscopic observation of the surface of the optical recording media with recorded information by using a semiconductor laser device with an oscillation wavelength of 658 nm revealed that random signals containing fine marks with minimum mark length of less than 1.0 μm were formed on the tracks at a relatively high density.

Example 15

Optical Recording Medium

Any one of the methine dyes represented by Chemical Formulae 26 to 28 as light-absorption materials was added to TFP to give a concentration of 1.2% (w/v), and further admixed with a conventionally used formazan metal complex as a light-tolerance improver in an amount of 5.0% (w/w) against the light-absorption material, followed by heating the mixture for a while and being energized with ultrasonic for dissolution. According to conventional manner, the solution was membrane filtered, homogeneously applied in a rotatory manner over either side of a CD-R disk substrate (12 cm in diameter, 1.2 mm in thickness, track pitch of 1.6 μm), and dried to form a recording layer, 200 nm in thickness. Thereafter, pure silver was evaporated over the substrate to give a layer, 100 nm in thickness, by spattering method to form a reflection layer closely attached to the recording layer, to which was then homogeneously applied in a rotatory manner with "DAICURE CLEAR SD1700", a product name of ultra violet hardening resin commercialized by DIC Corporation, Tokyo, Japan, irradiated with ultra violet to form protection layers closely attached to the reflection layer. Thus, three types of optical recording media were prepared. When tested similarly as in Example 13, any of the optical recording media according to the present invention exerted substantially the same levels of electric properties, such as recording sensitivity, modulation property, reflection percentage, and jitter, as those in Example 13.

The optical recording media, having improved electric properties such as recording sensitivity, modulation property, reflection percentage, and jitter, have a recording capacity of over 600 MB and record large amounts of information such as document information, image information, voice information, and other digital information by using a light pickup by a visible light with a wavelength of shorter than 850 nm, particularly, a laser beam with a wavelength of around 750 to 800 nm. An electron microscopic observation of the surface of the optical recording medium with recorded information by using a semiconductor laser device with an oscillation wavelength of 780 nm revealed that random signals containing fine marks with minimum mark length of less than 1.0 μm were formed on the tracks at a relatively high density.

Example 16

Optical Recording Medium

Any one of the methine dyes represented by Chemical Formulae 21 and 24 as light-absorption materials was added to TFP to give a concentration of 1.0% by weight, and further admixed with a commonly used formazan metal complex as a light-tolerance improver in an amount of 20.0% by weight against the light-absorption material and energized with ultrasonic for dissolution. The resulting solution was applied over a HD DVD-R disk substrate (12 cm in diameter, 0.6 mm in thickness, track pitch of 0.4 μm) by spin coating method, provided with a silver reflection membrane, 120 nm in thickness, and attached to a back plate, 0.6 mm in thickness, using an ultra violet hardening resin to obtain two types of optical recording media.

Using a tester with a wavelength of 405 nm and an NA 0.65, produced by Pulstech Industries Co., Ltd., Shizuoka, Japan, the optical recording media were recorded at a line speed of 6.61 m/s and a minimum mark length of 0.2 μm. The test for recording and reproducing were conducted in accordance with the method of HD DVD-R standard Ver. 1.0 defined by DVD Forum and evaluated by PRSNR (Partial Response SNR) specified in the standard.

As the result from the evaluation test, the optical recording media of the present invention showed the LOW-TO-HIGH mechanism and gave a PRSNR value of 15 far exceeding the standard level of 15 when operated at its maximum recording power.

The data indicates that all of the optical recording media of the present invention have a recording capacity of 15 GB or over and can record large amounts of information such as document information, image information, voice information, and other digital information by using a laser element with an oscillation wavelength of about 405 nm. It is understood that the optical recording media of the present invention fulfill the desired durability requisite for optical recording media in general and the acceleration test shows that the information once recorded can be read out for a relatively long period of time even when repeatedly read out or even after repeatedly exposed to environmental light.

POSSIBILITY OF INDUSTRIAL APPLICABILITY

As described above, the present invention was made based on the establishment of novel methine dyes and the findings of their industrially useful characteristics. The methine dyes have improved light tolerance, efficiently absorb the light in the ultra violet and the infrared regions, exert satisfactory solubility with no actual problem in use against variety of organic solvents, and improved thermal tolerance, and therefore they can be quite advantageously used as light-absorption materials which use light energy in the ultra violet region to the infrared region in various fields of, for example, information recordings, solar energy generations, electric equipments, electric communications apparatuses, optical equipments, clothes, building/bedding/decorating products, health goods, and agricultural materials.

Particularly, the methine dyes have desired sensitivity to the light with wavelengths of 350 to 850 nm in the field of information recording can be advantageously useful, for example, as light-absorbing materials, which correspond to increased recording speed as high as at least 8× write drive, and which construct recording layers in high-density optical recording media with a recording capacity of 15 to 23.3 GB per side, such as DVD-Rs, BD-Rs, and HD DVD-Rs. Also the methine dyes of the present invention can be advantageously used as light-absorbing materials for constructing the recording layers in optical recording media such as commercialized CD-Rs and DVD-Rs, corresponding to a recording speed of 1× and 4× write drives.

The invention claimed is:

1. A methine dye which comprises an atomic group represented by General Formula 2:

General Formula 2:

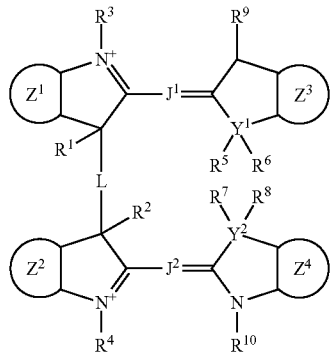

wherein in General Formula 2, $Z^1$ to $Z^4$ each independently represent aromatic rings which may have substituents, $R^1$, $R^2$, $R^5$, $R^6$, $R^7$ and $R^8$ each independently represent hydrogen atoms or appropriate substituents, $R^3$, $R^4$, $R^9$ and $R^{10}$ are the same or different hydrocarbon groups which may have substituents, any two of the substituents for $R^5$ to $R^8$ or of the hydrocarbons for $R^9$ and $R^{10}$ may be linked together via a divalent linking group, L represents a divalent linking group which may have a substituent, $J^1$ and $J^2$ each independently represent monomethine or polymethine chains, which may have substituents and/or cyclic structures, $Y^1$ and $Y^2$ each independently represent carbon atoms or hetero atoms, and when $Y^1$ and/or $Y^2$ are hetero atoms, part or the whole of $R^5$ to $R^8$ do not exist.

2. An optical recording medium, which comprises the methine dye of claim 1.

3. The methine dye of claim 1, which is the compound represented by Chemical Formula 36:

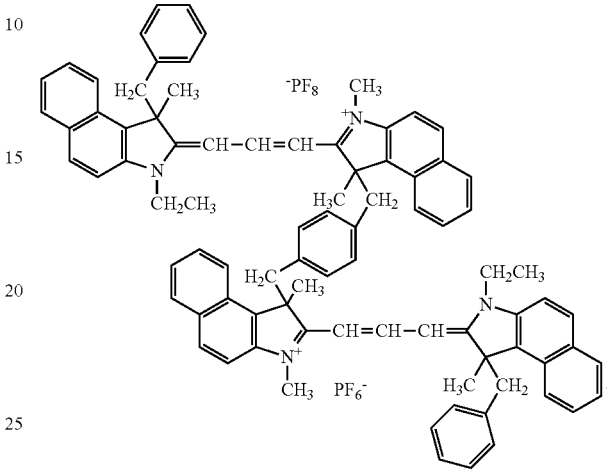

4. The optical recording medium, wherein the methine dye is the compound represented by Chemical Formula 36:

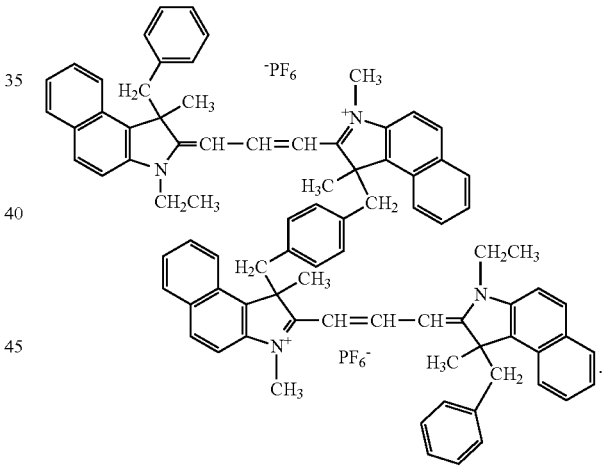

* * * * *

UNITED STATES PATENT AND TRADEMARK OFFICE
CERTIFICATE OF CORRECTION

| | | |
|---|---|---|
| PATENT NO. | : 8,049,018 B2 | |
| APPLICATION NO. | : 12/293066 | |
| DATED | : November 1, 2011 | |
| INVENTOR(S) | : Dan-Oh | |

It is certified that error appears in the above-identified patent and that said Letters Patent is hereby corrected as shown below:

At column 46, claim 3, the counter anion in chemical formula 36 that reads "-PF8" should be changed to read --PF6--.

Signed and Sealed this
Twenty-seventh Day of March, 2012

David J. Kappos
*Director of the United States Patent and Trademark Office*